US011311297B2

(12) United States Patent
Gordon et al.

(10) Patent No.: US 11,311,297 B2
(45) Date of Patent: Apr. 26, 2022

(54) DEVICES FOR APPROXIMATING TISSUE AND RELATED METHODS OF USE

(71) Applicant: Boston Scientific Scimed, Inc., Maple Grove, MN (US)

(72) Inventors: Lindsay Gordon, San Francisco, CA (US); Sylvie Stacy, Bessemer, AL (US); Johannah Van Der Plas, Maineville, OH (US); Anita R. Kalra, Greenville, SC (US); Eamon Doyle, Sierra Madre, CA (US); David Wurtz, Boulder, CO (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 261 days.

(21) Appl. No.: 16/520,566

(22) Filed: Jul. 24, 2019

(65) Prior Publication Data
US 2019/0343523 A1    Nov. 14, 2019

Related U.S. Application Data

(63) Continuation of application No. 15/439,524, filed on Feb. 22, 2017, now Pat. No. 10,441,284, which is a
(Continued)

(51) Int. Cl.
*A61B 17/08* (2006.01)
*A61B 17/10* (2006.01)
(Continued)

(52) U.S. Cl.
CPC .......... *A61B 17/08* (2013.01); *A61B 17/0057* (2013.01); *A61B 17/083* (2013.01);
(Continued)

(58) Field of Classification Search
CPC .............. A61B 17/0057; A61B 17/068; A61B 17/0682; A61B 17/0684; A61B 17/0686; A61B 17/072; A61B 17/08; A61B 17/083; A61B 17/10; A61B 17/1114; A61B 17/115; A61B 17/1155; A61B 17/29; A61B 2017/00278; A61B 2017/00349; A61B 2017/00575; A61B 2017/00579;
(Continued)

(56) References Cited

U.S. PATENT DOCUMENTS 4,791,707 A    12/1988  Tucker
4,796,627 A    1/1989   Tucker
(Continued)

FOREIGN PATENT DOCUMENTS

EP    0380874 A1    8/1990
JP    12-015065     10/1937
(Continued)

OTHER PUBLICATIONS

PCT Invitation to Pay Additional Fees and, Where Applicable, Protest Fee and Partial International Search Report for PCT/US2010/049092, dated Mar. 18, 2011 (7 pages).
(Continued)

*Primary Examiner* — Robert A Lynch
(74) *Attorney, Agent, or Firm* — Bookoff McAndrews, PLLC

(57) ABSTRACT

Devices for approximating multiple tissue edges internal to a body are disclosed.

20 Claims, 23 Drawing Sheets

Related U.S. Application Data continuation of application No. 14/577,199, filed on Dec. 19, 2014, now Pat. No. 9,610,081, which is a continuation of application No. 12/883,245, filed on Sep. 16, 2010, now Pat. No. 8,945,157.

(60) Provisional application No. 61/272,457, filed on Sep. 25, 2009.

(51) Int. Cl.
*A61B 17/00* (2006.01)
*A61B 90/00* (2016.01)
*A61B 17/02* (2006.01)

(52) U.S. Cl.
CPC .......... *A61B 17/10* (2013.01); *A61B 17/0218* (2013.01); *A61B 2017/00278* (2013.01); *A61B 2017/00349* (2013.01); *A61B 2017/00579* (2013.01); *A61B 2017/00584* (2013.01); *A61B 2017/00588* (2013.01); *A61B 2017/00637* (2013.01); *A61B 2017/00659* (2013.01); *A61B 2017/00668* (2013.01); *A61B 2017/00818* (2013.01); *A61B 2017/081* (2013.01); *A61B 2090/037* (2016.02)

(58) Field of Classification Search
CPC .......... A61B 2017/00584; A61B 2017/00588; A61B 2017/00637; A61B 2017/00668; A61B 2017/00659; A61B 2017/00818; A61B 2017/081; A61B 2017/088; A61B 2017/1157; A61B 2017/2926; A61B 2090/037; A61F 5/0083; A61F 5/0086; A61F 5/0089
See application file for complete search history.

(56) References Cited

U.S. PATENT DOCUMENTS

| | | |
|---|---|---|
| 5,478,354 A | 12/1995 | Tovey et al. |
| 5,609,598 A | 3/1997 | Laufer et al. |
| 5,782,861 A | 7/1998 | Cragg et al. |
| 5,976,161 A | 11/1999 | Kirsch et al. |
| 6,786,913 B1 | 9/2004 | Sancoff et al. |
| 2004/0220593 A1 | 11/2004 | Greenhalgh |
| 2005/0021057 A1 | 1/2005 | St. Goar et al. |
| 2005/0124912 A1 | 6/2005 | Griego et al. |
| 2005/0182426 A1 | 8/2005 | Adams et al. |
| 2005/0267529 A1 | 12/2005 | Crockett et al. |
| 2006/0135988 A1 | 6/2006 | Peterson |
| 2007/0197858 A1 | 8/2007 | Goldfarb et al. |
| 2007/0244510 A1 | 10/2007 | Weizman et al. |
| 2008/0147184 A1 | 6/2008 | Lattouf |
| 2008/0287988 A1 | 11/2008 | Smith et al. |
| 2008/0294179 A1 | 11/2008 | Balbierz et al. |
| 2009/0149870 A1 | 6/2009 | Jugenheimer et al. |
| 2010/0016883 A1 | 1/2010 | Christoudias |
| 2013/0306704 A1 | 11/2013 | Balbierz et al. |

FOREIGN PATENT DOCUMENTS

| | | |
|---|---|---|
| JP | 2001309920 A | 11/2001 |
| JP | 2005-534347 A | 11/2005 |
| JP | 2006-528911 A | 12/2006 |
| JP | 2008514244 A | 5/2008 |
| JP | 4390414 B2 | 12/2009 |
| WO | 91/13590 | 9/1991 |

OTHER PUBLICATIONS

English translation of Office Action dated May 14, 2014, in counterpart Japanese Patent Application No. 2012-530941 (8 pages).

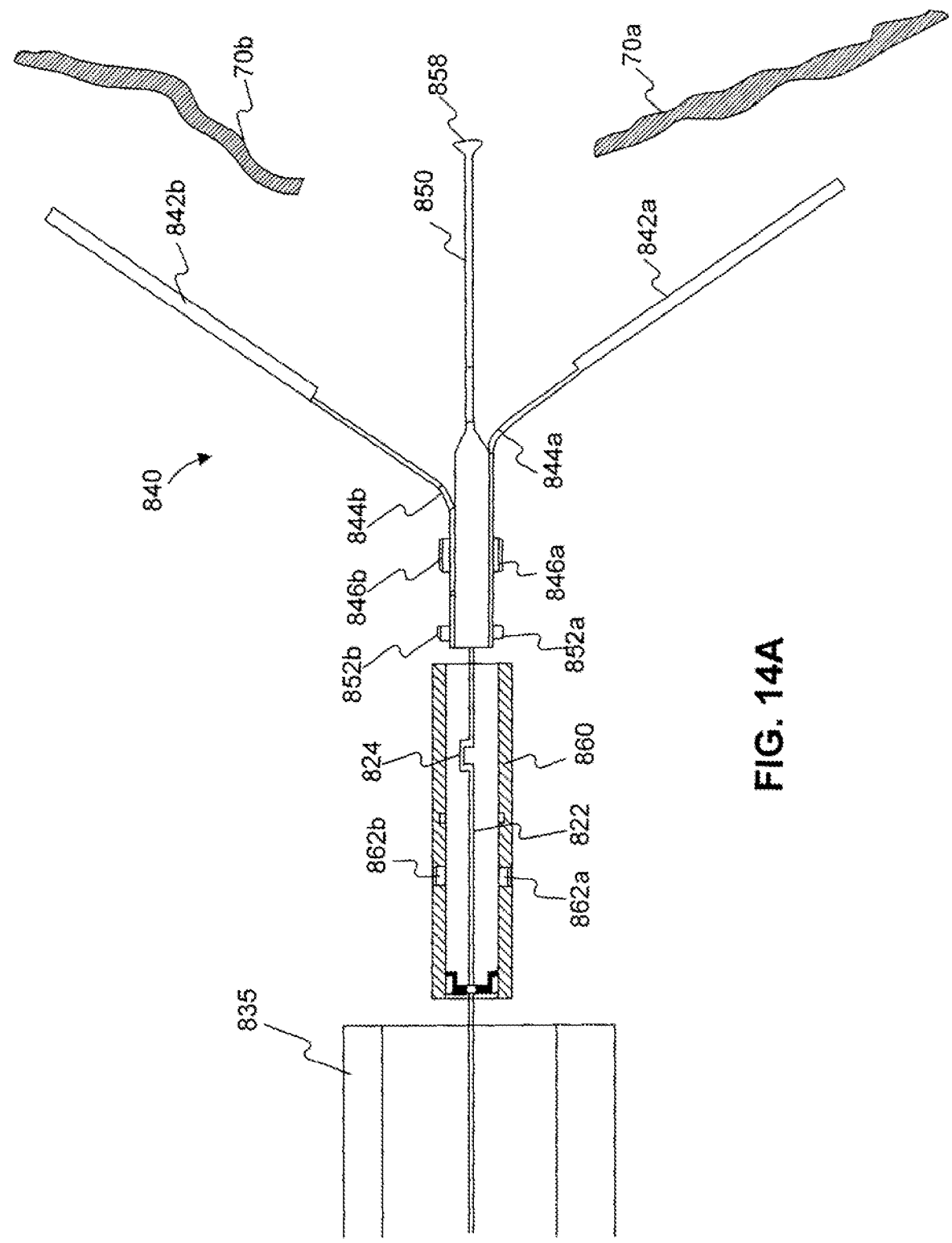

DEVICES FOR APPROXIMATING TISSUE AND RELATED METHODS OF USE

CROSS-REFERENCE TO RELATED APPLICATIONS

The present application is a continuation of U.S. application Ser. No. 15/439,524, filed Feb. 22, 2017, which is a continuation of U.S. application Ser. No. 14/577,199, filed on Dec. 19, 2014, now U.S. Pat. No. 9,610,081, which is a continuation of U.S. application Ser. No. 12/883,245, filed on Sep. 16, 2010, now U.S. Pat. No. 8,945,157, which claims priority from U.S. Provisional Patent Application No. 61/272,457, filed on Sep. 25, 2009, the entireties of which are incorporated herein by reference.

FIELD OF THE INVENTION

Embodiments of the present invention relate to tissue approximation clips used during surgery. In particular, embodiments of the present invention relate to clips that may be used to bring tissue edges proximate to one another to close apertures created during surgery.

BACKGROUND OF THE INVENTION

During recent years, a major drive in surgery has been the development and application of minimally invasive approaches to traditional operations. In general surgery, an emphasis has been on laparoscopic techniques, which can now be applied to a majority of intra-abdominal procedures. The resulting reduction in trauma to the abdominal wall has a positive impact on patients undergoing abdominal operations.

More recently, there has been interest in less traumatic transluminal endoscopic surgical procedures. In transluminal endoscopic surgery, an endoscope is used to deliberately breach (puncture) the wall of the stomach or other organ to work within a body cavity such as the peritoneal cavity. Single point access surgery, is an advanced minimally invasive surgical procedure in which the surgeon operates almost exclusively through a single entry point, such as the patient's navel. In a transluminal endoscopic surgical procedure, a flexible endoscope (along with the required surgical tools) is inserted into the stomach, for example, through a natural anatomic opening. Once the endoscope reaches the access site in the stomach or other organ, the wall of the organ is punctured and the endoscope advanced into the body cavity where the remotely controlled surgical tools can be used to perform delicate surgical procedures. When the surgical procedure is completed, the endoscope and the tools are withdrawn through the aperture in the organ wall and the aperture is closed.

Although minimally invasive surgeries have tremendous potential in reducing trauma associated with surgical procedures, several important developments should be pursued before these procedures can be widely employed. One such development is a safe and effective method of approximating two tissue edges in the body cavity so that they can be stapled or otherwise joined together. Existing tissue approximation techniques only enable joining of two tissue edges which are already in close proximity to one another. There is often a need to bring one tissue edge from a first location to the location of a second tissue edge in order to join them, and thereby, initiate healing.

SUMMARY OF THE INVENTION

An embodiment of the invention may include a device to approximate multiple tissue edges. The device may include a plurality of jaws each having a first end and a second end coupled at the first ends. The device may also include a fixed element located between the jaws. A jaw may be independently moved with respect to the fixed element from an open configuration to a closed configuration. The open configuration may be a configuration where a second end of a jaw is located away from a fixed element and the closed configuration may be a configuration where a second end of a jaw mates with a fixed element to grasp a tissue edge between a jaw and a fixed element.

Various embodiments of the invention may include one or more of the following aspects: one end of a fixed element may be coupled to a jaw at the first end; a first end may be coupled to a distal end of an elongate member, and a proximal end of an elongate member may be coupled to an actuation device, an actuation device may be configured to move a jaw with respect to a fixed element, and an elongate member may be configured to pass through a lumen of an endoscope; a fixed element may include barbs; and a barb may be configured to pierce a tissue edge between a jaw and a fixed element.

An embodiment of the invention may also include a device to approximate multiple tissue edges. The device may include a plurality of jaws each including a first end and a second end. The jaws may be coupled to each other at their first ends and configured to transform from an open configuration to a closed configuration. The open configuration may be a configuration where a second end of a jaw is located away from a second end of another jaw. The closed configuration may be a configuration where a second end of a jaw is proximate a second end of another jaw. The device may also include one or more tools configured to pass between the jaws. A tool may be configured to move relative to the jaws and grasp a tissue edge between the jaws.

Various embodiments of the invention may also include one or more of the following aspects: a first end of a jaw may be coupled to a distal end of an elongate member, and an elongate member may be configured to pass through a lumen of an endoscope; a first end may include a hole and an elongate member may extend through the hole; a tool may be coupled to a distal end of an elongate section, a proximal end of an elongate section may be coupled to an actuation device configured to be located external to the body, and an actuation device may be configured to control a tool to grasp a tissue edge.

An embodiment of the invention may also include a device to approximate tissue edges. The device may include a plurality of jaws coupled to each other at a first end, and a midsection located between the jaws. The midsection may include a plurality of forks coupled together. A fork may be configured to move to mate with a jaw and grasp a tissue edge between the fork and a jaw.

Various embodiments of the invention may also include one or more of the following aspects: a midsection coupled to a distal end of an elongate member, and a proximal end of an elongate member coupled to an actuation device, an actuation device may be configured to move a fork; a distal end of an elongate member may include a groove, and a first end of a jaw may be located proximate a groove; and the jaws may be joined at a first end, a first end may include a hole through which a midsection passes.

An embodiment of the invention may also include a device to approximate tissue edges. The device may include a first jaw including a proximal end and a distal end, and a second jaw including a proximal end and a distal end. A first jaw and a second jaw may be configured to transform from an open configuration to a closed configuration. The open configuration may be a configuration where distal ends of the jaws are located away from each other, and the closed configuration may be a configuration where the distal ends of the jaws are located proximate to each other. The device may also include a barb including a first end and a second end. The first end may be coupled to a jaw. The device may also include a feature on a jaw, the feature may be configured to receive a second end of a barb when the jaws are in the closed configuration.

Various embodiments of the invention may also include one or more of the following aspects: a first jaw may move relative to a second jaw; a feature may include a hole; a jaw may include elements configured to increase the compliance of a jaw; a barb may be configured to transform from a first configuration to a second configuration, the first configuration may be a restricted configuration where a second end of a barb is proximate a jaw, and the second configuration may be a deployed configuration where a second end of a barb is distal to a first jaw; a second end of a barb may include a sharp tip; a barb may include a plurality of spikes protruding from a surface of a barb; first and second jaws may be coupled to an end of an elongate member, the elongate member may be configured to pass through a lumen of an endoscope.

An embodiment of the invention may also include a method of approximating tissue edges. The method may include delivering a clip to a location of a tissue edge. The clip may include a plurality of jaws and a fixed element, wherein a jaw may be moved from an open configuration to a closed configuration. The method may also include grasping a tissue edge between a jaw and a fixed element, and moving a clip along with a grasped tissue edge to a location proximate to a second tissue edge. The method may further include grasping a tissue edge between a second jaw and a fixed element, and releasing a clip with a tissue edge grasped between the jaws.

Various embodiments of the invention may also include one or more of the following aspects: a fixed element may be located between the jaws; a jaw may be independently moved with respect to a fixed element; a closed configuration of a jaw may be a configuration where a jaw mates with a fixed element, and an open configuration may be a configuration where a jaw may be disposed away from a fixed element; delivering a clip may include delivering a clip through a lumen of a device extending into a body; extending a clip outside a lumen may transform a jaw into an open configuration and retracting a clip into a lumen may transform a jaw into a closed configuration; the method may further include retracting a clip into a lumen to transform a jaw to a closed configuration; grasping a tissue edge between a jaw and a fixed element; and grasping another tissue edge between a jaw and a fixed element; a fixed element may include a barb configured to pierce a tissue edge.

An embodiment of the invention may also include another method of approximating tissue edges. The method may include delivering a clip including multiple jaws to a location of the tissue edges, and delivering a first tool to a location of the tissue edges. The method may also include grasping a tissue edge using a first tool, and retracting a first tool with a grasped tissue edge to a location in between the jaws, and delivering a second tool to a location of the tissue edges. The method may further include grasping a second tissue edge using a second tool, and retracting the second tool with a grasped tissue edge to a location in between the jaws to approximate the tissue edges.

Various embodiments of the invention may also include one or more of the following aspects: a jaw may include a proximal end and a distal end and may be configured to transform from an open configuration to a closed configuration, the open configuration may be a configuration where a distal end of the jaws are located away from each other, and the closed configuration may be a configuration where a distal end of the jaws are proximate to each other; delivering a clip may include delivering a clip through a lumen of a device extending into a body; the lumen may include one of a lumen of a catheter or a working lumen of an endoscope; extending a clip outside the lumen may transform a jaw into an open configuration, and retracting a clip into a lumen may transform the clip into a closed configuration; the method may further include extending a clip outside a lumen to transform a jaw into an open configuration, and retracting a clip into a lumen to transform a clip to a closed configuration and grasp a tissue edge between the multiple jaws; the method may further include releasing a tissue edge from a first tool and a tissue edge from a second tool, and releasing a clip with the clip grasping the tissue edges; piercing the grasped tissue edges with a barb to join the tissue edges together; releasing a tissue edge from a first tool and a second tissue edge from a second tool, and releasing a barb with a barb piercing a tissue edge.

An embodiment of the invention may also include another method of approximating tissue edges. The method may include delivering a clip to a location of the tissue edges, the clip may include jaws coupled together, at least one jaw movable relative to another other jaw from an open configuration to a closed configuration, and a barb coupled to a jaw. The method may also include transforming a movable jaw to a closed configuration to grasp a tissue edge between the jaws, and piercing the tissue edge with a barb. The method may further include moving a clip along with a grasped tissue edge to a location proximate to another tissue edge, and transforming a movable jaw with the grasped tissue edge to an open configuration. The method may also include transforming a movable jaw to a closed configuration to grasp a tissue edge between the jaws, the tissue edge may be pierced by a barb.

Various embodiments of the invention may also include one or more of the following aspects, a barb may pierce a tissue edge while a movable jaw may transform to a closed configuration to grasp a tissue edge; the closed configuration may be a configuration where a distal end of each of the jaws is proximate to each other, and the open configuration may be a configuration where a distal end of each of the jaws is located away from each other; a barb may include a first end and a second end, the first end may be coupled to a jaw and a second end may form a sharp point; a second end of a barb may be proximate a first jaw; the method may further include moving a barb to a deployed orientation, wherein a second end of a barb may be positioned to pierce a tissue edge after transforming the movable jaw to a closed configuration to grasp a tissue edge; the method may also include compliance features on a jaw; a barb may include a plurality of spikes protruding from a surface of a barb; releasing a clip with a clip grasping the tissue edges; uncoupling a barb from a clip with the barb piercing the tissue edges; delivering a clip includes delivering a clip through a lumen of a device extending into the body, the device may include one of a catheter or an endoscope.

An embodiment of the invention may also include another method of approximating tissue edges. The method may include delivering a clip mounted on an elongate member to a location of a tissue edge, the elongate member may include multiple forks at a distal end, and a clip including multiple jaws located about the forks, wherein a fork may be moved between a closed configuration and an open configuration. The method may also include moving a fork to an open configuration to grasp a tissue edge between a fork and a jaw, and moving a clip along with a grasped tissue edge to a location proximate to a tissue edge. The method may also include moving a fork to an open configuration to grasp a tissue edge between a fork and a jaw, and releasing a clip with a clip grasping a tissue edge.

Various embodiments of the invention may also include one or more of the following aspects: delivering a clip may include delivering a clip through a lumen of a device extending into a body; extending a clip outside a lumen may transform a jaw into an open configuration and retracting a clip into a lumen may transform a jaw into a closed configuration, the open configuration may be a configuration where a distal end of the jaws is located away from each other, and the closed configuration may be a configuration where a distal end of the jaws is located proximate to each other; extending a clip outside a lumen to transform a jaw into an open configuration, and retracting a clip into a lumen to transform a jaw to a closed configuration and grasp the tissue edges between the jaws and the forks; retracting forks from between the jaws in the closed configuration; delivering a clip includes locating a clip on a groove of an elongate member, the groove may be located proximate a distal end of an elongate member; locating a second clip on a groove after releasing a clip; a fork may be independently moved with respect to another fork between a closed configuration and an open configuration; and a plurality of clips may be mounted on an elongate member.

An embodiment of the invention may also include another method of approximating tissue edges. The method may include delivering a clip including multiple jaws to location of tissue edges, wherein the jaws are configured to transform between an open configuration and a closed configuration, delivering a capture tool into the body, and snagging a tissue edge using a capture tool. The method may also include retracting a capture tool to drag a tissue edge between the jaws, transforming the jaws to a closed configuration to grasp a tissue edges between the jaws, and releasing a clip with a clip grasping the tissue edges.

Various embodiments of the invention may also include one or more of the following aspects: delivering a clip includes delivering a clip through a lumen of a device extending into a body; extending a clip outside a lumen transforms the jaws into an open configuration, and retracting the clip into a lumen transforms the jaws into a closed configuration, the open configuration may be a configuration where a distal end of the jaws is located away from each other, and the closed configuration may be a configuration where a distal end of the jaws are located proximate to each other; extending a clip outside a lumen to transform the jaws into an open configuration, and retracting a clip into a lumen to transform the jaws to a closed configuration; delivering a capture tool into the body may include delivering a first capture tool into the body in between the jaws, and delivering a second capture tool into the body in between the jaws; snagging tissue edges may include snagging a tissue edge using a first capture tool, and snagging a tissue edge using a second capture tool; retracting a capture tool may include retracting a capture tool to drag a tissue edge to a location between the jaws, and retracting a capture tool to drag a second tissue edge to a location between the jaws; delivering a clip includes delivering a clip mounted on an elongate member into a body, and releasing a clip includes sliding a clip off an elongate member.

BRIEF DESCRIPTION OF THE DRAWINGS

The accompanying drawings, which are incorporated in and constitute a part of this specification, illustrate embodiments of the invention and together with the description, serve to explain the principles of the invention.

FIGS. 14A-14F are illustrations of another embodiment of a clip and a method of using a clip.

DESCRIPTION OF THE EMBODIMENTS

Reference will now be made in detail to exemplary embodiments of the invention, examples of which are illustrated in the accompanying drawings. Wherever possible, the same reference numbers will be used throughout the drawings to refer to the same or like parts. Even so, the invention is not limited to the specific embodiments and drawings listed herein.

Figure 1:
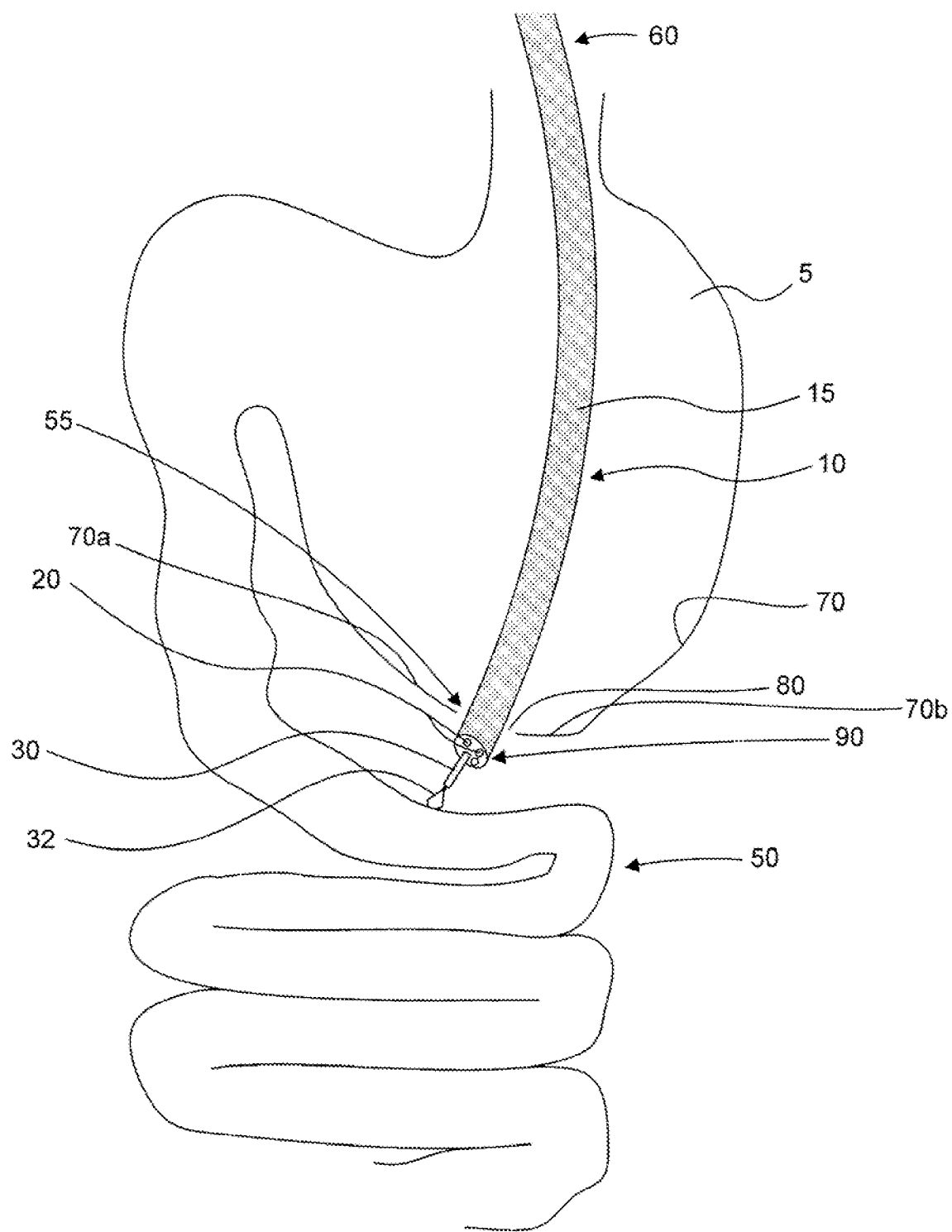
FIG. 1 is a schematic view of an endoscope performing an exemplary endoscopic surgical procedure.

FIG. 1 depicts an exemplary endoscope 10 performing an exemplary endoscopic surgery. Non-limiting examples of the endoscopic surgery may include choecsyectomies, gastrojejunostomies, stomach resections, polypectomies, vasectomies, tubal ligations, etc. In one embodiment, an endoscope 10, or other suitable device such as a guide tube or a catheter, may be inserted into the stomach 5 through the esophagus. Endoscope 10 may make an aperture 80 on organ wall 70, pass through the aperture 80, and operate at a work site. The work site could include, for instance, part of the small intestine 50. It should be emphasized that the illustrated application of the endoscope 10 in FIG. 1 is exemplary only, and that the inventions of the current disclosure may be applied to any surgical application or medical procedure known in the art.

Endoscope 10 may include an elongate member 15 extending between a proximal end 60 and a distal end 90. In the configuration depicted in FIG. 1, the proximal end 60 may include the end of endoscope 10 external to the body and the distal end 90 may include the end of endoscope 10 internal to the body. A plurality of lumens 20 may run longitudinally through endoscope 10. The lumens 20 may extend between the proximal end 60 external to the body and the distal end 90 internal to the body. In some embodiments, the longitudinal axes of the lumens may be substantially parallel to the longitudinal axes of the endoscope 10.

The lumens 20 may provide access to devices and facilities that may aid in performing a diagnostic or therapeutic task inside the body. In general, the lumens may be of any shape or geometry. In some embodiments, some or all lumens may be lined with a polymeric or another layer or coating to facilitate use. These lumens 20 may include one or more of, among others, an aspiration lumen, an irrigation lumen, an illumination lumen, a viewing lumen, and working lumens. The illumination lumen may include devices at the distal end configured to illuminate the work site. These devices may include, among others, bulbs, LED's, fiber optic cables and light guides. The viewing lumen may include devices (such as a camera) at the distal end 90, configured to deliver an image of the work site external to the body. In some embodiments the camera may be a digital camera, such as a CCD or a CMOS camera. The illumination and the viewing lumens may also include cables that may run from the distal end 90 to the proximal end 60.

The irrigation lumen may be configured to facilitate fluid flow from the proximal end 60 to the distal end 90. In some embodiments, the proximal end 60 of the irrigation lumen may be attached to a source of fluid, and the distal end 90 may be attached to a nozzle to alter fluid flow. The aspiration lumen may be configured to facilitate suction and/or fluid flow through it. In some embodiments, fluid may flow from the proximal end 60 to the work site through the irrigation lumen. The fluid may then be removed from the work site through the aspiration lumen. In some embodiments, the aspiration lumen may also be configured to remove biological material along with fluid from the work site. For instance, a tissue sample along with fluid (delivered to the work site via the irrigation lumen) may be extracted out of the body through the aspiration lumen.

The working lumen may include a hollow cavity configured to deliver an endoscopic instrument 30 to the work site. The endoscopic instrument 30 may include a surgical tool configured to operate at the work site while being remotely controlled from outside the body. The surgical tool may be configured as an end effector 32 that may be attached at the distal end of the endoscopic instrument 30. In general, the working lumen may have any suitable shape, size, and configuration. In some embodiments, the working lumen may have a substantially circular cross-section, while in other embodiments, the shape of the working lumen may be configured to pass the end effector 32 of the endoscopic instrument 30 through it. Some embodiments of the endoscope may include a plurality of working lumens to deliver multiple surgical tools to the work site.

In addition to the end effector 32, an endoscopic instrument 30 may also include a mechanism to operate the end effector 32 from outside the body. This mechanism may include linkage that connects the end effector 32 to an actuation device (not shown) at the proximal end. This linkage may operate the end effector 32 in response to actuation by the actuation device. For example, in some embodiments, the end effector 32 may include forceps with a pair of jaws rotably coupled to each other. The linkage, in this embodiment, may include a pair of cables, each coupled to a jaw of the forceps at the distal end and to the actuation device at the proximal end. Actuation of the actuation device may move one of the cables relative to the other, causing the jaws of the forceps to open and close.

The end effector 32 may include any medical instrument that may be used in conjunction with the endoscope 10. In some embodiments, the end effector 32 may be a purely mechanical medical instrument (for example, biopsy forceps, baskets, graspers, snares, surgical knifes, needles, suturing instruments, etc.), while in others, the end effector 32 may also include devices with parts driven by an electric current (for instance, electric motors, heating elements for cutting or cauterizing, hemostasis devices, radio frequency ablation devices, etc.). The end effector 32 may also include a surgical instrument, such as a trocar, used to puncture an internal surface of the body.

In the exemplary transluminal endoscopic surgery illustrated in FIG. 1, the endoscope 10 may be inserted into the body through a natural anatomic opening (such as, mouth, anus, and vagina, etc.) or through the body percutaneously. When the distal end 90 of the endoscope 10 is proximate to an internal surface (such as, organ wall 70), an endoscopic instrument 30, for example, an end effector suitable for puncturing organ wall 70, may be delivered to the distal end 90 of the endoscope 10 via the working lumen. The end effector may be used to puncture the organ wall 70. Puncturing the organ wall 70 may create cut multiple tissue edges. These tissue edges may include a first tissue edge 70a and a second tissue edge 70b. Once the organ wall 70 is punctured, the endoscopic tool 30 with the end effector 32 may be withdrawn from the working lumen, and the endoscope 10 inserted into the abdominal cavity through the aperture 80. When the distal end 90 of the endoscope 10 is positioned at the desired work site, for instance, the intestine 50, an endoscopic instrument 30 with an end effector 32 configured to perform a desired task may be delivered to the work site through the working lumen.

The desired operations may be performed at the work site using an end effector 32. If more than one tool is required to complete the desired task, other desired end effectors 32 may also be delivered to the work site. After completion of the desired operations, the endoscope 10 and tools may be retracted from the abdominal cavity through aperture 80. Aperture 80 may now be closed by joining the separated tissue edges (for example, first tissue edge 70a and second tissue edge 70b) to initiate the healing process. To close aperture 80, two or more tissue edges spatially dislocated from each other may have to repositioned close to each other (referred to herein as "approximated") before they can be joined together. A tissue approximation clip according to embodiments of the present disclosure may now be delivered to the access site 55 or aperture via the working lumen. The approximation clip may be configured to grasp tissue edges at different locations at the access site 55, bring them in close proximity to each other, and join the tissue pieces together.

The tissue approximation clips of the present disclosure may be made of any suitable biocompatible material. In general, a clip may be comprised of a material having any type of constitutive behavior, such as, a material exhibiting a behavior which is elastic, plastic, elastic-perfectly plastic, hyper-elastic, etc. In some embodiments, a bioabsorbable material may be included. It is also contemplated, that in some embodiments, a clip may be comprised of multiple components made of multiple materials. In some embodiments, a clip may comprise a shape memory alloy (SMA). Non-limiting examples of SMA's included in the clip include alloys of titanium-palladium-nickel, nickel-titanium-copper, gold-cadmium, iron-zinc-copper-aluminum, titanium-niobium-aluminum, iron-manganese-silicon, nickel-titanium, nickel-iron-zinc-aluminum, copper-aluminum-iron, titanium-niobium, etc. In some embodiments, a clip may comprise or consist of nitinol.

In general, clips of the present disclosure may be made by any process known in the art. In some embodiments, arms or jaws of the clip may be formed by a bending operation of material, and holes or cavities through the clip may be formed by a machining or laser drilling operation. In some embodiments, the clip may be subjected to heat treatment or other microstructure modification metallurgical operations during or after the fabrication process. In embodiments, where the clip may comprise a shape memory alloy, the material of the clip or the manufactured clip may be subjected to metallurgical treatments. These metallurgical operations may enable the clip to transform from a first configuration to second configuration by the application of heat or other stimuli. The first configuration may correspond to a martensitic phase and the second configuration may correspond to an austenitic phase of a shape memory alloy. Several embodiments of clips of the present disclosure and their method of operation will now be described in the following paragraphs.

Figure 2A:
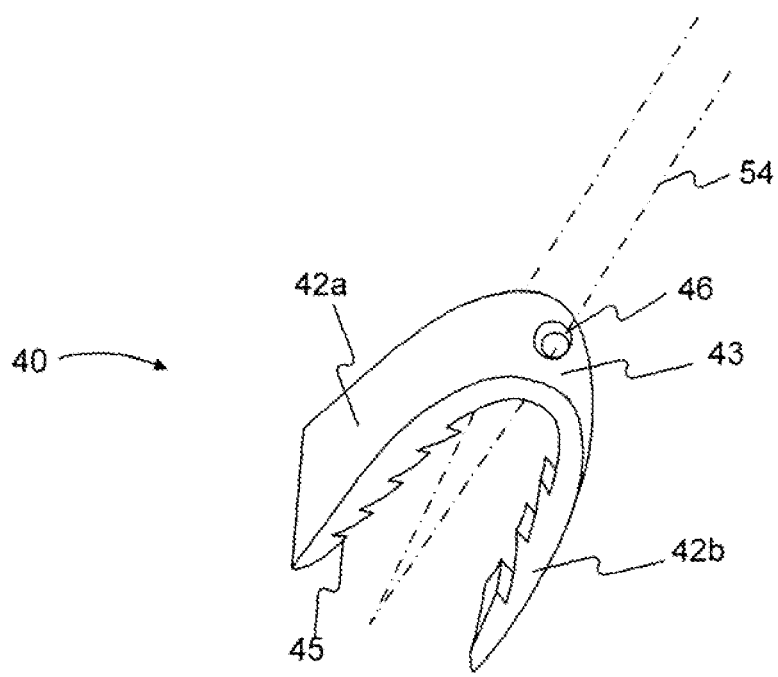
FIGS. 2A and 2B are schematic views of exemplary clips for closing an aperture created during an endoscopic surgical procedure.

FIG. 2A illustrates an embodiment of the tissue approximation clip 40 that may be delivered to aperture 80. Clip 40 may comprise a unitary construction, and may resemble a strip of material folded along a plane 54, at an angle to, and passing through a center of the strip. Clip 40 may have two jaws, a second jaw 42a and a first jaw 42b, joined by a midsection 43. Clip 40 may further include a through-hole 46 therethrough. An inside surface of the two jaws may have an irregular or corrugated surface such as teeth 45. Although the surface corrugation of clip 40 is depicted as teeth 45, any kind of surface configurations may also be used. In some embodiments, the second jaw 42a and the first jaw 42b may be symmetric about plane 54 which may pass through a center of through-hole 46. However, it is contemplated that, in some embodiments, the two jaws may not be symmetric. The through-hole 46 may have any shape. In some embodiments, the through-hole 46 may have a circular shape.

Figure 2B:
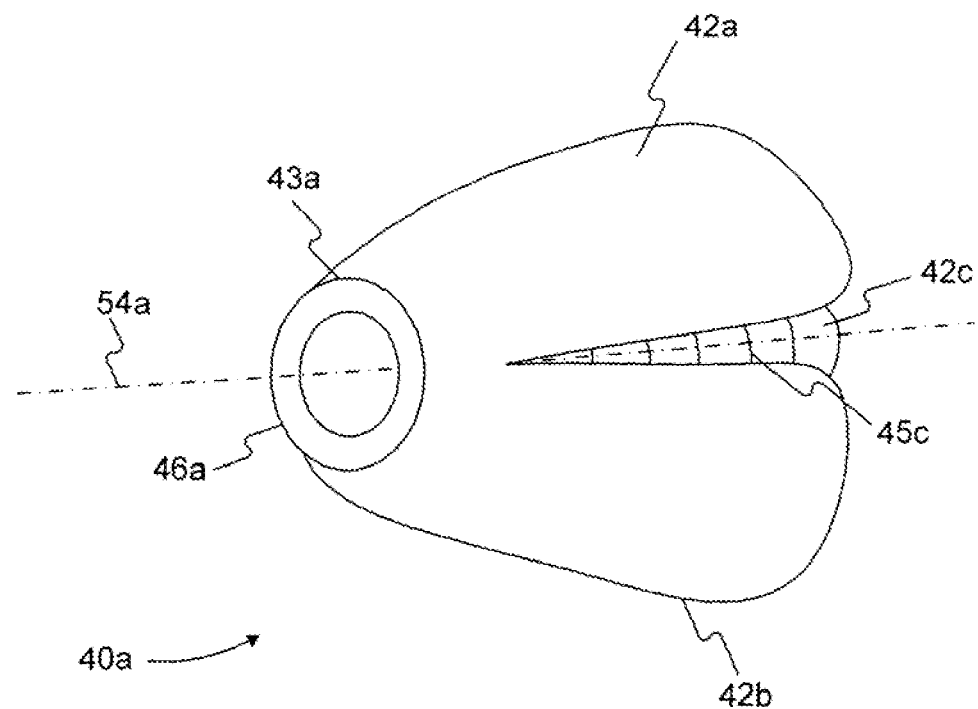

Although clip 40 is depicted as having two jaws (second jaw 42a and first jaw 42b) and an unvarying cross-section along a thickness direction, it is contemplated that clip 40 may have other configurations. For instance, in the embodiment of the clip 40a depicted in FIG. 2B, clip 40a may resemble the shape of a tulip having at least three jaws, a second jaw 42a, a first jaw 42b, and a third jaw 42c. The jaws may be substantially shaped like petals of the tulip. Other embodiments of the clip 40a may have a different number of jaws. As in the embodiment illustrated in FIG. 2A, the jaws of clip 40a may be joined by a midsection 43a with a through-hole 46a centrally located therein. An axis 54a may pass through a center of the through-hole 46a, and an inside surface of the three jaws may have a corrugated surface or teeth 45a.

FIGS. 3A-H illustrate an exemplary method of using a clip 40 to approximate tissue edges and join them. One or more clips 40 may be loaded on a push-rod 22 and delivered to the access site 55 though a tubular catheter 35. The clips 40 may be constrained to be in a closed configuration while inside the catheter 35. At access site 55, clip 40 still mounted on push-rod 22 may be extended from within the catheter 35. When clip 40 emerges from within the catheter 35, a constraint which holds the clip in a closed configuration may be released, and the clip may expand to an open configuration. It is also contemplated that in some embodiments, a constrain may force the clip to an open configuration when clip 40 emerges from catheter 35. The access site 55 may have one or more tissue edges, a first tissue edge 70a and a second tissue edge 70b, created while traversing through organ wall 70. The first tissue edge 70a may be grasped between one jaw and the push-rod 22 and dragged to the location of the second tissue edge 70b. The second tissue edge 70b may then be grasped between another jaw and the push-rod 22. Push-rod 22 may then be pulled out from between clip 40 and retracted into catheter 35, releasing clip 40 with the tissue edges clutched between its jaws. The released clip 40 may now approximate first tissue edge 70a and second tissue edge 70b. Each step of some embodiments of this method of operating clip 40 will now be described in greater detail.

Figure 3A:
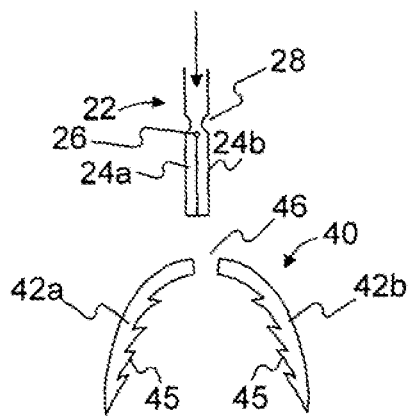
FIGS. 3A-3H are illustrations of an exemplary method of using a clip.
Figure 3B:
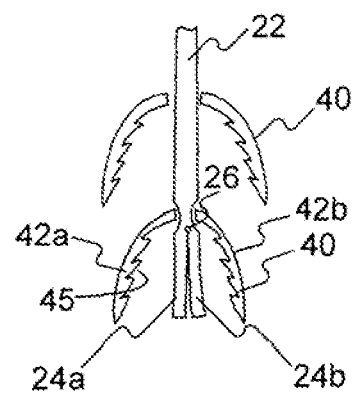

FIGS. 3A and 3B illustrate mounting a clip 40 on push-rod 22. Push-rod 22 may be an elongate member having a groove 28 near its distal end. Past groove 28, the push-rod may include a hinge with two forks, a second fork 24a and a first fork 24b. The two forks may form the distal most part of push-rod 22. Hinge 26 may allow each fork to open independent of the other. In some embodiments, opening of the forks may be a purely mechanical operation, while in other embodiments, energy such as heat and/or electricity may be used alone or in combination with mechanical energy to open the forks. While opening, second fork 24a and first fork 24b may rotate about the hinge 26. While closing, the forks may rotate in the opposite manner. Although the forks are described as rotating about hinge 26 while opening and closing, it is also contemplated that in some embodiments, the two forks may move in another manner with respect to each other while opening and closing. Opening and closing of the forks may be controlled by an actuation mechanism at the proximal end of push-rod 22. This actuation mechanism may include linkages that connect the forks to the actuation mechanism. These linkages may open and close the forks in response to activation by the actuation device. In some embodiments, linkages may include cables coupled to each fork. In these embodiments, pulling the cable connected to a fork may open the fork. In other embodiments, a push rod may push the forks open. In some embodiments, the forks may be biased to remain in a closed configuration with a spring. In these embodiments, pulling the cable may open the forks, and releasing the cable may close the forks.

The distal end of push-rod 22 may be inserted into through-hole 46 to load one or more clips 40 on the push-rod, such that the jaws of the loaded clips face the forks. In some embodiments, the diameter of through-hole 46 and push-rod 22 may be such that frictional resistance between the mating surfaces of the clips and the push-rod retains clips 40 on the surface of push-rod 22. The clip closest to the two forks may be located on push-rod 22 such that through-hole 46 of the clip may be positioned on groove 26. While clip 40 is in this position, opening a fork of the push-rod may rotate the fork until it rests on teeth 45 of a jaw of clip 40. For instance, when clip 40 is located on groove 26, opening first fork 24b may rotate this fork in a counterclockwise direction until the first fork rests against teeth 45 of first jaw 42b (see FIG. 3E). Further opening of the first fork 24b may push this fork against first jaw 42b.

Figure 3C:
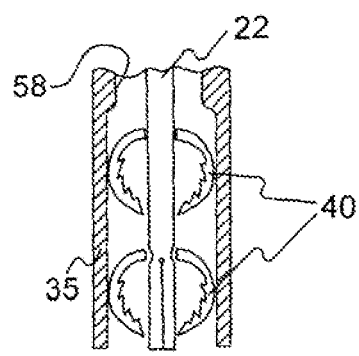

Push-rod 22 along with the loaded clips may be inserted into a catheter 35 as seen in FIG. 3C. Catheter 35 may comprise a hollow tube with an external diameter sized to be inserted into a working lumen of endoscope 10. The jaws of clip 40 may deflect inwards from an open configuration to a closed configuration while being inserted into catheter 35. The internal diameter of a distal end of catheter 35 may be such that the clips in a closed configuration may slide longitudinally within the catheter freely. Push-rod 22 may be inserted into catheter 35 such that all the loaded clips are positioned within the catheter, and a proximal end of push-rod 22 protrudes from a proximal end of catheter 35. At some distance near the distal end, the internal surface of catheter 35 may have a flange 58 designed to stop the longitudinal movement of clip 40. In some embodiments, flange 58 may be a region of reduced diameter of catheter 35. It is also contemplated that the flange 58 can have other configurations, such as, a protrusion of a size that prevents the passage of a loaded clip past the protrusion.

In some embodiments, the distance of flange 58 from the distal most end of catheter 35 may be factor in determining the number of clips 40 that may be loaded on a push-rod positioned within the catheter. The internal dimensions of catheter 35 may be configured to facilitate locating a clip on groove 28 of push-rod 22. For instance, pulling push-rod 22 in a proximal direction from the proximal end of catheter 35 may move the push-rod, along with the loaded clips, into the catheter towards the proximal end. During this movement, a loaded clip may run into flange 58. The flange may thus prevent longitudinal movement of the clip towards the proximal end. Further pulling of the push-rod towards the proximal end may cause the push-rod to slide on the through-hole 46, thereby positioning the clip on the groove.

Figure 3D:
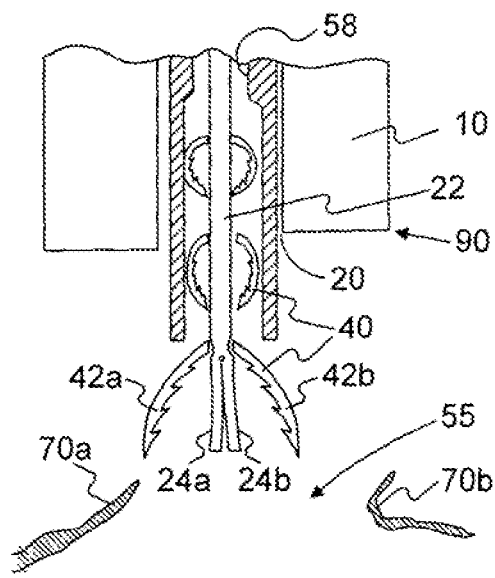

The catheter 35 with the inserted push-rod 22 may now be delivered to the access site 55 through a working lumen of the endoscope 10. The endoscope may be positioned within the body such that the distal end 90 of the endoscope 10 is proximate the access site 55. FIG. 3D illustrates one embodiment of delivery of the clip 40 to an access site 55. The catheter 35 may be delivered such that loaded clip 40 extends from the distal end 90 of the endoscope 10. While thus positioned, pushing the push-rod 22 into the catheter 35 from the proximal end may extend the push rod 22 with the loaded clip 40 out of the distal end of the catheter 35. When the push-rod 22 is pushed into the catheter 35 to extend the clip 40 positioned on the groove 28 from the distal end of the catheter 35, the jaws of the clip 40 may spring back to its open configuration. It is contemplated that in some embodiments, the jaws may not return completely to their pre-deformed configuration, but may retain some plastic deformation. The distal end 90 of the endoscope 10 and/or the distal end of the catheter 35 may now be maneuvered to position extended clip 40 proximate one tissue edge (first tissue edge 70a or second tissue edge 70b).

Figure 3E:
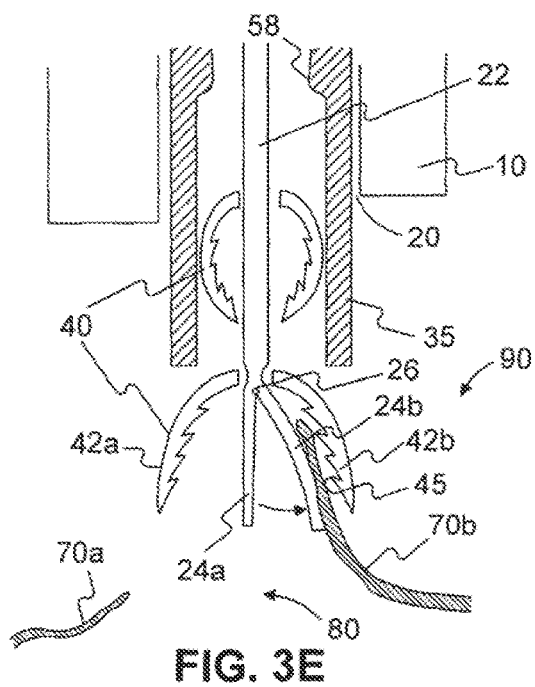
Figure 3F:
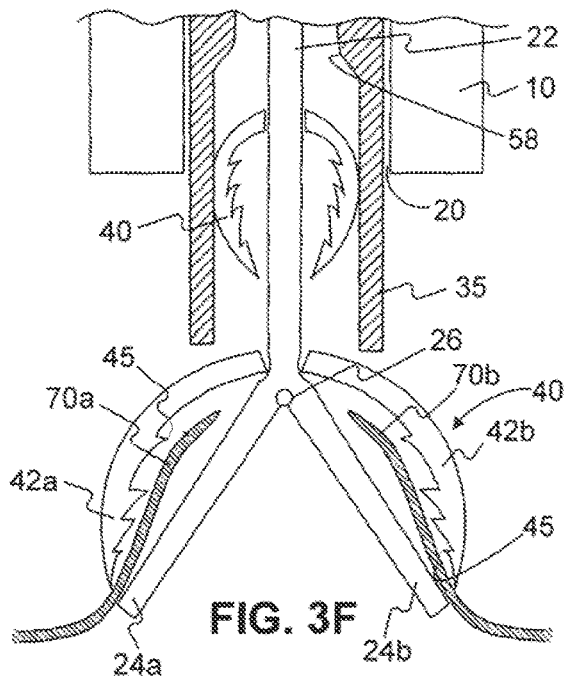

Clip 40 may now be used to grasp these separated tissue edges. FIG. 3E illustrates grasping second tissue edge 70b between the first fork 24b and the first jaw 42b. To grasp the second tissue edge 70b, the clip 40 may be maneuvered to locate the second tissue edge 70b between the first fork 24b and the first jaw 42b. When clip 40 is suitably positioned, the actuation device may be used to open first fork 24b. Opening the first fork 24b may rotate the first fork 24b about the hinge 26 in a counterclockwise direction. The opening first fork 24b may force the trapped second tissue edge 70b against the teeth 45 of the first jaw 42b thereby firmly grasping the second tissue edge 70b between the first fork 24b and the first jaw 42b. While thus grasping the second tissue edge 70b, the endoscope 10 or catheter 35 may be maneuvered to the location of the first tissue edge 70a. When the clip 40 is suitably positioned proximate the first tissue edge 70a, the second jaw 42a may be opened to grasp the first tissue edge 70a between the second jaw 42a and the first fork 24a. FIG. 3F illustrates clip 40 grasping the first tissue edge 70a.

Figure 3G:
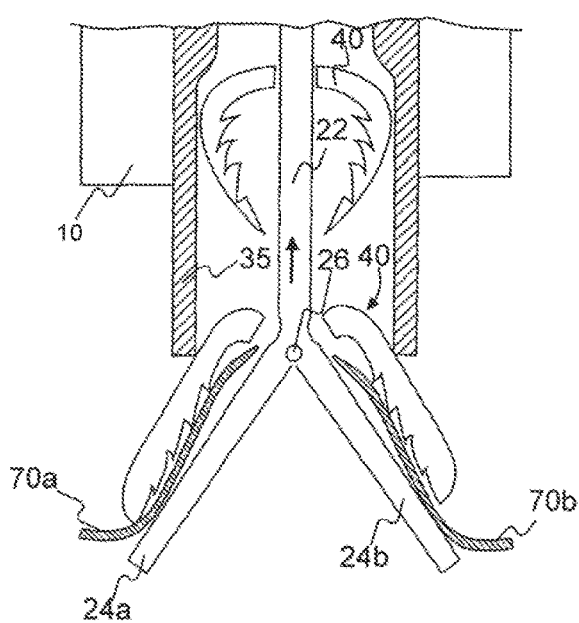

With the two tissue edges firmly grasped between the jaws and the forks, push-rod 22 may be pulled towards the proximal end to force clip 40 towards the catheter 35. FIG. 3G illustrates one embodiment of the clip 40 being pulled towards the catheter 35. While the clip 40 is being retracted into the catheter 35, the open jaws of the clip are pushed inwards by the walls of the catheter 35. The reaction force of the catheter 35 on the open jaws of the clip may deform the jaws with the tissue edges and the forks sandwiched between the jaws. In some embodiments, part or all of clip 40, with the tissue edges sandwiched between its jaws, may enter the distal end of catheter 35 as the push-rod 22 is pulled into the catheter 35.

Figure 3H:
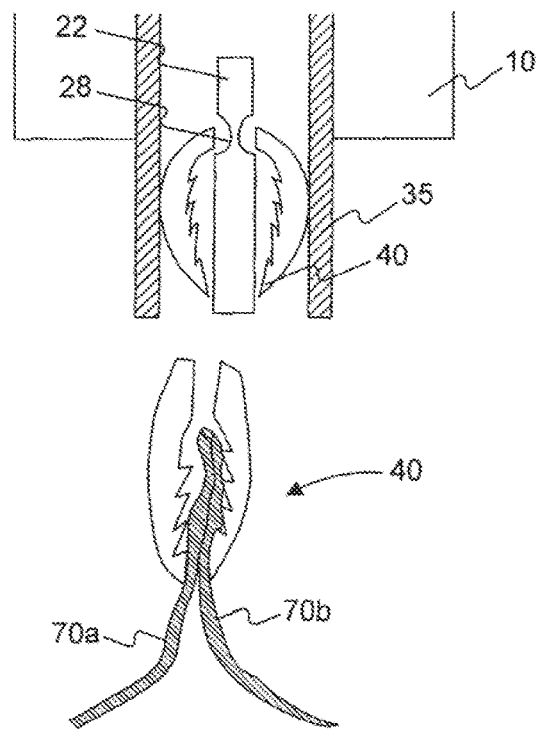

In some embodiments, further pulling of the push-rod 22 from the proximal end of the catheter 35 may further pull the forks out from between the jaws of the clip 40, leaving the tissue edges sandwiched between the deformed jaws of the clip. In embodiments where a part of the deformed clip 40 enters the distal end of catheter 35 upon retraction of the push-rod 22, retracting the catheter 35 away from the access site 55 may stretch the organ wall 70 to allow the clip 40 to be pulled out of the distal end of the catheter 35 with the first tissue edge 70a and second tissue edge 70b sandwiched between its jaws. FIG. 3H illustrates a deformed clip 40 with the tissue edges grasped between its jaws. Clip 40 may thus close aperture 80 by joining the two tissue edges together. The action of retracting the push-rod 22 into catheter 35 may also position another loaded clip 40 in the groove 28 of the push-rod 22 as described previously.

Although the description above describes the method of closing a puncture with two tissue edges using clip 40, the same general approach can be used to close an aperture 80 having more than two tissue edges. To close a puncture with more than two tissue edges, a clip with multiple jaws may be used. For instance, clip 40a with three jaws depicted in FIG. 2B, may be used to close an aperture 80 with three tissue edges. In this embodiment, the push-rod 22 may include three forks that may be independently opened and closed from outside the body. The clip 40a may be loaded on the push-rod 22 and delivered to the access site 55 as described earlier. At the access site 55, the first tissue edge may be grabbed between a jaw and a fork and dragged to the location of the second tissue edge. A second tissue edge may then be grabbed between a second jaw and a fork. The distal end of the catheter 35 may then be maneuvered to the location of a third tissue edge, where the third tissue edge may be grabbed between the third fork and the jaw. Push rod 22 may then be retracted into the catheter to deform the jaws of clip 40a as discussed earlier. The push-rod 22 may be further retracted to extract the forks from between the jaws, thereby leaving the tissue edges pressed together by the deformed jaws. Although the description above describes a clip having jaws equal to the number of forks, this is not a requirement. That is, in some embodiments, the number of jaws of a clip may be different than the number of forks.

It is also contemplated that a device with two jaws (such as clip 40 depicted in FIG. 2A) may be used to close an aperture with more than two tissue edges. In such an application, two or more tissue edges may be grabbed between a jaw and a fork. A first tissue edge may be firmly embedded in the teeth 45 of the jaw so that it may not be released when the jaw is opened to grasp a second tissue edge.

Figure 4:
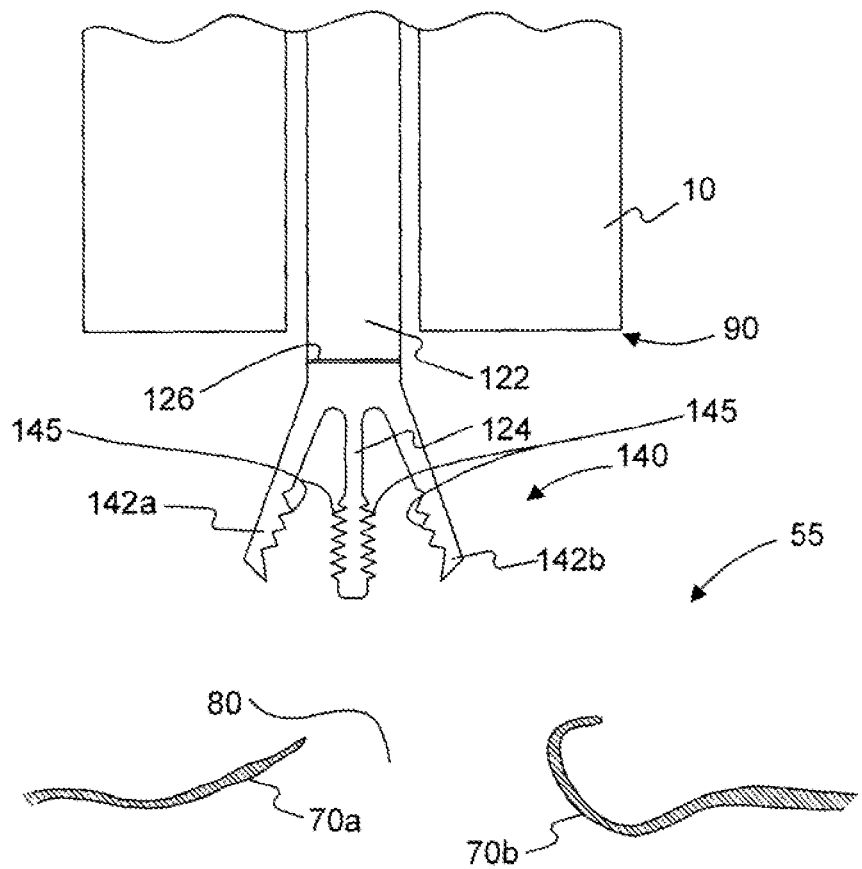
FIG. 4 is a schematic view of another embodiment of a clip.

FIG. 4 illustrates another embodiment of a tissue approximation clip 140 that may be used to close the aperture 80. Clip 140 of FIG. 4 may be attached to a distal end of an elongate member 122, and may be delivered to the access site 55 through the working lumen of the endoscope 10. In some embodiments, the elongate member 122 with the clip 140 may be delivered to the access site 55 via a catheter inserted into the working lumen. The elongate member 122 may connect the clip 140 to an actuation device attached to the proximal end thereof. The elongate member 122 may include mechanisms, such as links or cables, that may allow the actuation device to operate the clip 140. These actuation mechanisms may be similar to those discussed with reference to clip 40 of FIG. 3A, or may be different. The clip 140 may protrude from the distal end of the endoscope 10 to operate on the aperture 80.

Clip 140 may include three jaws—a first jaw 142a, a second jaw 142b, and a fixed center jaw 124. The jaws may have a corrugated surface, teeth 145, or other surface modifications on its facing sides. Similar to the opening left and right forks of the embodiment shown in FIGS. 3A-3H, the first jaw 142a and the second jaw 142b may be movable and may be opened and closed using the actuation mechanism. Closing the first jaw 142a may actuate this jaw about a hinge 126 until the teeth 145 on its surface presses against the teeth 145 on the fixed center jaw 124. And, closing the second jaw 142b may actuate this jaw about the hinge 126 until its teeth 145 meets the teeth 145 of the center jaw 124. The jaws may be opened by actuating the jaws in the opposite direction. In some embodiments, the first jaw 142a and the second jaw 142b may be biased to remain in the closed configuration. In these embodiments, the jaws may be opened by applying an opening force to overcome the biasing force. The jaws may actuate to a closed configuration when the opening force is removed. In some embodiments, when a jaw is closed against the center jaw, teeth 145 on both jaws lock to keep the jaw in a closed configuration.

Figure 5A:
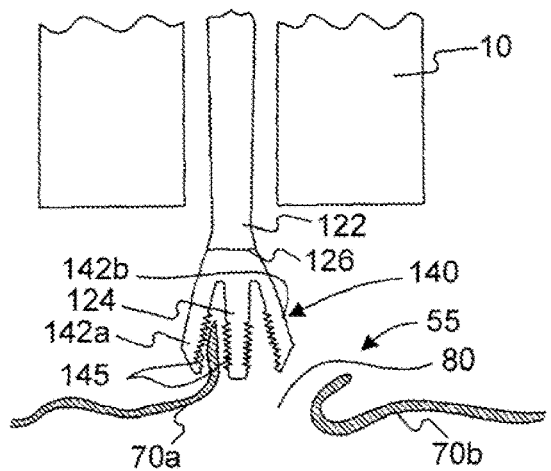
FIGS. 5A-5D are illustrations of an exemplary method of using a clip.
Figure 5B:
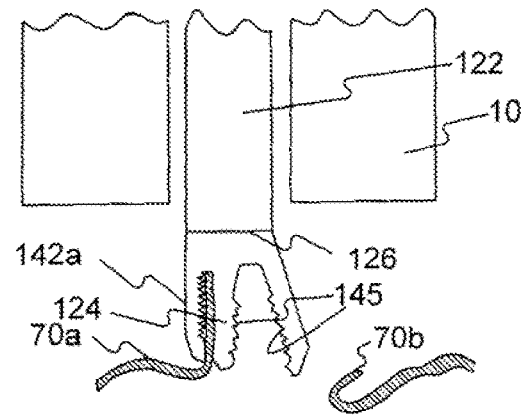

FIGS. 5A-D illustrate a method of using clip 140 to approximate tissue edges 70a and 70b and close the aperture 80. The clip 140 may be attached to the distal end of the elongate member 122 and delivered to the site of an aperture 80 via the working lumen of the endoscope 10. FIGS. 5A and 5B illustrate the clip 140 grasping a tissue edge 70a at the access site 55. At the access site 55, the endoscope 10 is maneuvered to position a first tissue edge 70a between the center jaw 124 and another jaw of the clip, for instance the first jaw 142a. The actuation device is then actuated to close the first jaw to firmly grasp the first tissue edge 70a between the first jaw 142a and the center jaw 124. In the closed configuration, the teeth 145 of the first jaw 142a and the center jaw 124 engage, thereby locking the first jaw 142a in the closed configuration.

Figure 5C:
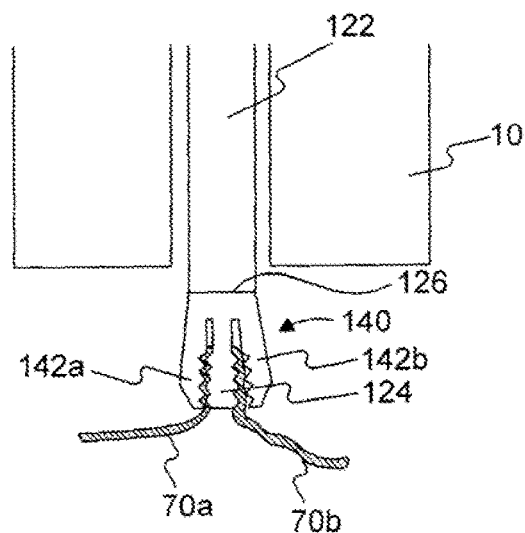
Figure 5D:
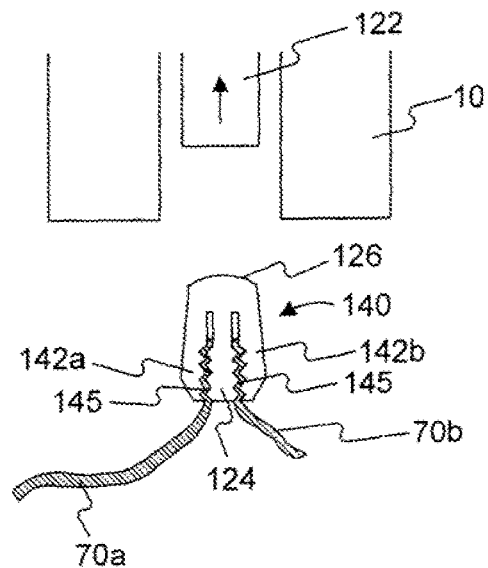

The clip 140 with the grasped first tissue edge 70a is maneuvered to the site of a second tissue edge 70b. The second tissue edge 70b is positioned between the second jaw 142b and the center jaw 124, and the second jaw 142b closed to lock the second tissue edge 70b between the teeth 145 of these jaws. FIG. 5C illustrates the first and second tissue edges 70a and 70b firmly grasped by clip 140. The clip 140 may thus close the aperture 80 by joining together the tissue edges that form the aperture 80. Once the tissue edges are thus joined, the clip 140 may be released. FIG. 5D illustrates the released clip 140. The released clip 140 may keep the aperture 80 closed allowing the natural healing process to grow fresh tissue around the joined tissue edges.

In general, a clip may be released from an elongate member by any means. In some embodiments a frangible link or an electrolysis link may be used to release a clip from an elongate member. Clip 140 also may be released from the elongate member by any other suitable method, including methods that use the actuation mechanism. In some embodiments, a clasp may retain the clip 140 on the distal end of the elongate member 122. In these embodiments, the actuation mechanism may operate the clasp to release the clip 140. In some embodiments, the distal end of the elongate member 122 may have threads that mate with threads on a mating face of the clip 140. In these embodiments, rotating the elongate member 122 about its longitudinal axis may unscrew the clip 140 from the elongate member 122, and release the clip 140.

Figure 6:
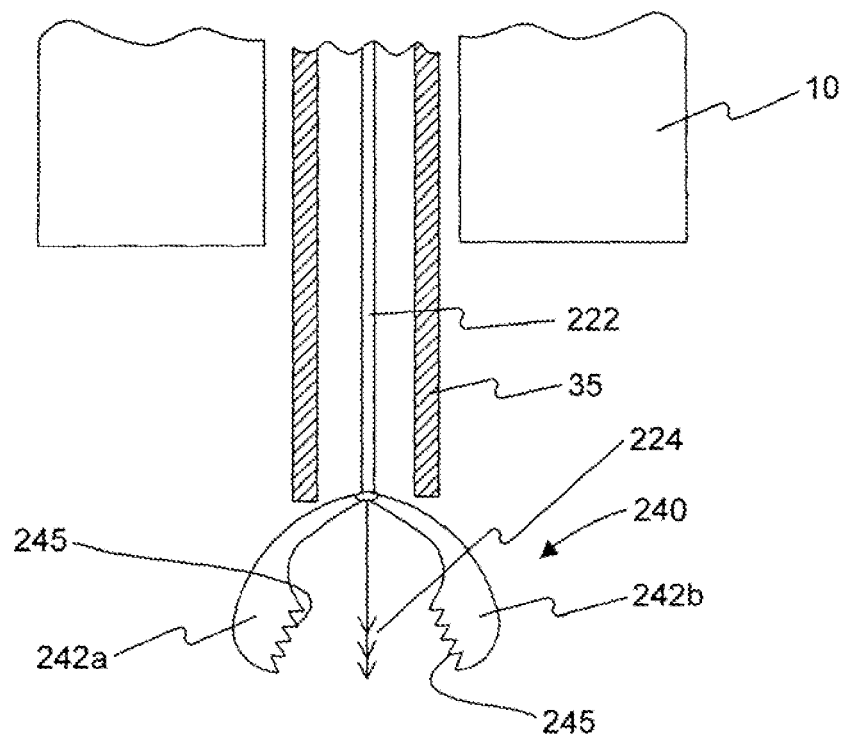
FIG. 6 is a schematic view of another embodiment of a clip.

FIG. 6 illustrates another embodiment of a tissue approximation clip 240 that may be used to close the aperture 80. Clip 240 may include a first jaw 242a and a second jaw 242b hinged to an elongate member 222 at hinges 226a and 226b (see FIG. 7A), respectively. The first jaw 242a and the second jaw 242b may also include teeth 245 or other surface irregularities on facing surfaces. The clip 242 may be located at the distal end of the elongate member 222, and may be delivered to an access site 55 within a catheter 35. The catheter 35 may be delivered to the access site 55 through a working lumen of an endoscope 10. The first jaw 242a and the second jaw 242b may be configured to slide individually on elongate member 222 to extend from the distal end of the catheter 35. A hook 224 having barbs, may also be located between the first jaw 242a and the second jaw 242b. The barbs may be sharp needle like features that protrude from the distal end of hook 224, or just a raised profile at the distal end of hook 224. Clip 240 may close aperture 80 by clamping the tissue edges between its jaws. FIGS. 7A-E illustrate a method of using clip 240 to approximate and join tissue edges.

Figure 7A:
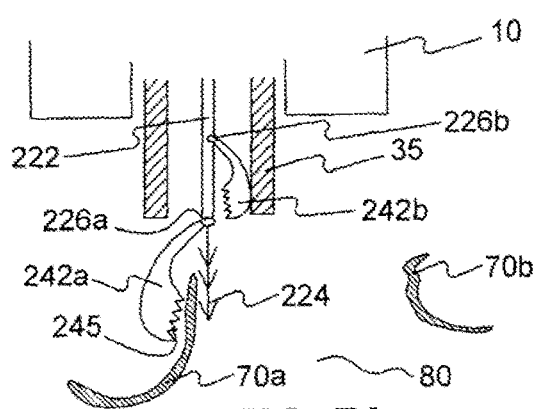
FIGS. 7A-7E are illustrations of an exemplary method of using a clip.
Figure 7B:
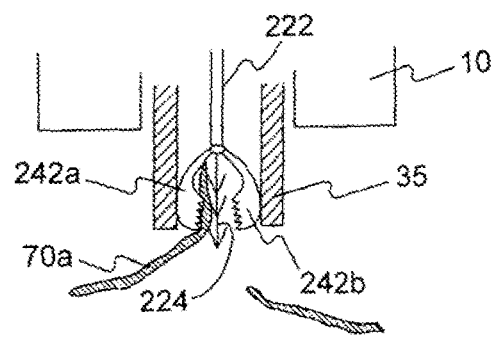

When the distal end of the catheter 35 is proximate the first tissue edge 70a, the first jaw 242a along with the hook 224 may be extended from within the catheter 35. The jaws may be biased to open when released from within the catheter 35. The catheter 35 and/or the endoscope 10 may be positioned to locate the first tissue edge 70a between the extended jaw and the hook 224. FIG. 7A shows device 240 with the first tissue edge 70a located between the first jaw 242a and the hook 224. When the tissue is appropriately positioned, the first jaw 242a along with hook 224 may be retracted into catheter 35. A catch or a feature on an inside surface of the catheter 35 may prevent the second jaw 242b from retracting further into catheter 35 when the first jaw 242a is retracted. Withdrawing the catheter 35 may force the first jaw 242a to a closed configuration, trapping the tissue between the jaw and the hook 224. FIG. 7B illustrates the clip 240 with the first tissue edge 70a grasped by the first jaw 242a and the hook 224. When the first jaw 242a closes over the first tissue edge 70a, the barbs of hook 224 and teeth 245 of first jaw 242a may lock, or cooperate together in another manner, to hold first tissue edge 70a firmly in place. In an embodiment of clip having sharp barbs and teeth, these barbs and teeth may pierce through the first tissue edge 70a to firmly hold the tissue edge between the jaw and the hook.

Figure 7C:
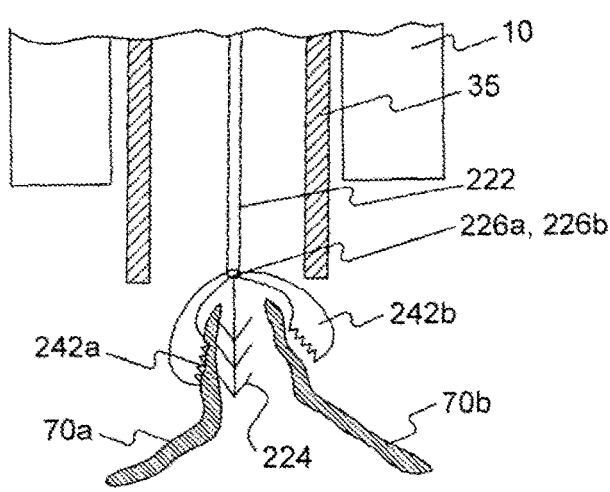
Figure 7D:
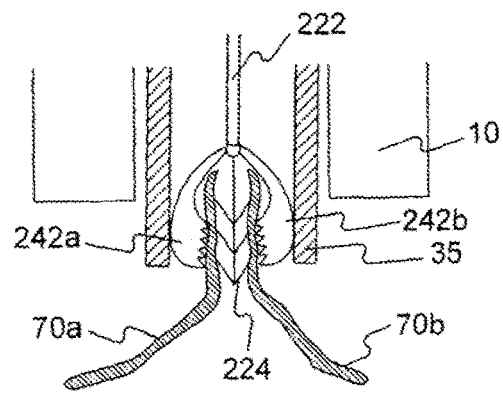

The endoscope 10 and/or catheter 35 may then be maneuvered to the location of the second tissue edge 70b, and the second jaw 242b extended from within the catheter 35 with first jaw 242a, hook 224, and first tissue edge 70a. The second jaw 242b may spring open and position itself over the second tissue edge 70b, when released from within the catheter 35. FIG. 7C shows clip 240 with the second tissue edge 70b located between the second jaw 242b and the hook 224. Once the jaw is appropriately positioned, the second jaw 242b may be retracted into the catheter 35 to close the second jaw 242b over the second tissue edge 70b. FIG. 7D illustrates the clip 240 in the retracted configuration. Closing the second jaw 242b over the second tissue edge 70b may also force the second tissue edge 70b against the hook 224, forcing the barbs and the teeth into the second tissue edge 70b.

Figure 7E:
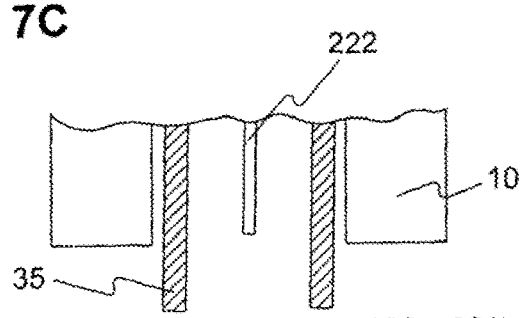
Figure 7E:
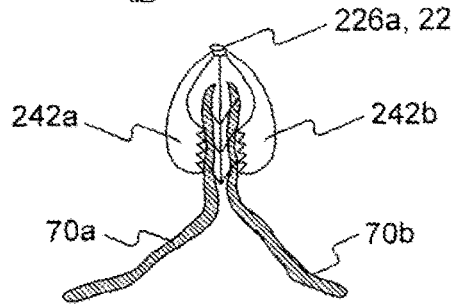

When the tissue edges are securely joined together, the clip 240 may be released and the catheter 35 withdrawn from the access site 55. FIG. 7E illustrates the release of the clip 240 from the catheter 35. The clip 240 along with the hook 224 may be separated from the elongate member 222 by activating a detachment mechanism on the actuation mechanism. In some embodiments, retracting the catheter 35 and/or elongate member 222 may stretch the organ wall 70 exerting a force on the clip. This force may break the connection of the clip to the elongate member 222, thereby releasing the clip 240 from the catheter 35. As indicated earlier, other detachment mechanisms may also be used to separate clip 240 from elongate member 222. The released clip 240 may remain in the body closing the aperture 80.

In some embodiments, only the hook 224, with the first tissue edge 70a and the second tissue edge 70b attached to its barbs, is released. In these embodiments, the actuation member activates a detachment mechanism releasing the hook 224 from the elongate member 222. In these embodiments, the hook 242 may hold the tissue edges together allowing subsequent tissue growth to permanently join the tissue edges together.

Figure 8A:
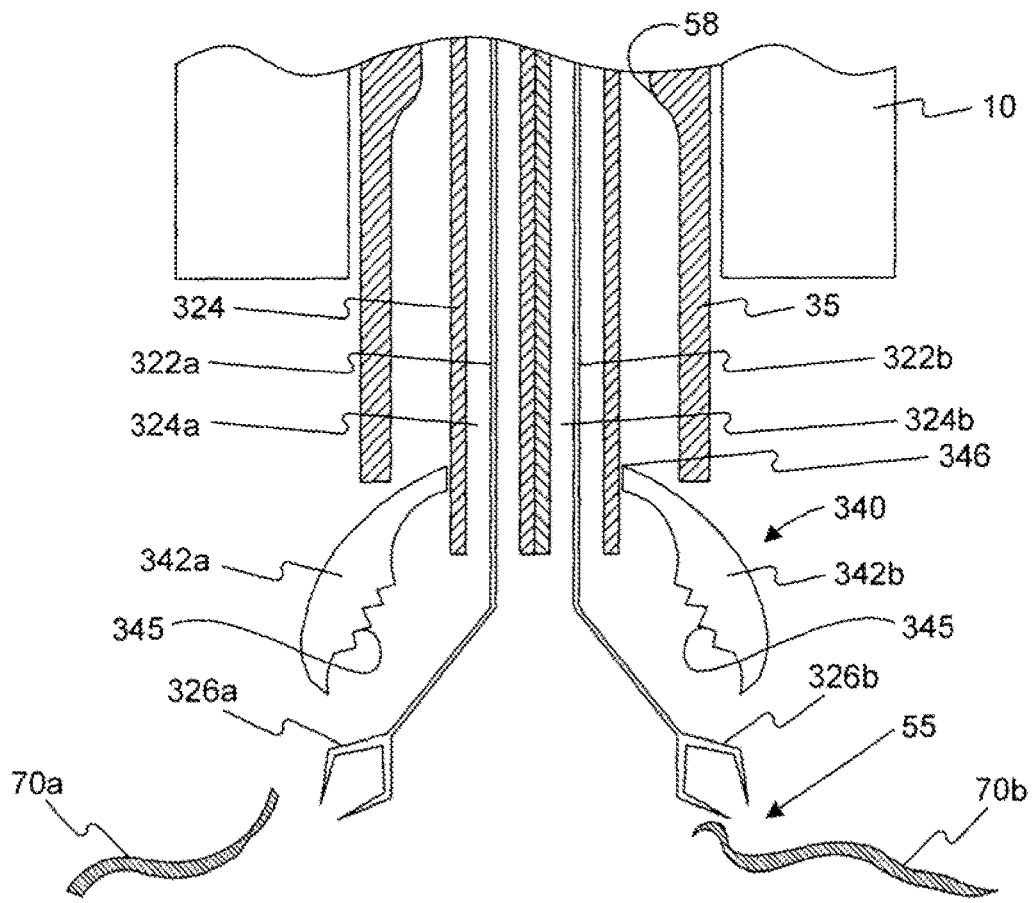
FIGS. 8A and 8B are illustrations of another embodiment of a clip and a method of using a clip.

FIG. 8A illustrates another embodiment of a clip 340 that may be used to close aperture 80. As in clip 40, clip 340 may have two jaws, a first jaw 342a and a second jaw 342b, joined by a midsection having a through-hole 346 therein. An inside surface of the two jaws may have a corrugated surface or teeth 345. The first jaw 342a and the second jaw 342b may be symmetric about a plane passing through a center of the through-hole 46. It is also contemplated that in some embodiments, clip 340 may have a different structure, for instance, an annular structure.

Clip 340 may be delivered to an access site 55, mounted on the surface of a sheath 324. The sheath 324 may be delivered to the access site 55 via a catheter 35 which slides within a working lumen of the endoscope 10. In some embodiments, the catheter 35 may be eliminated, and the sheath 324 may be delivered to the access site 55 directly via the working lumen. As described above with reference to other embodiments, clip 340 may transform from a closed configuration within the catheter 35 to an open configuration outside the catheter 35. When the sheath 324 is pulled into the catheter 35, the clip 340 may also retract into the catheter 35 until the longitudinal movement of the clip is blocked by flange 58. Flange 58 may be a feature on the internal surface of the catheter 35 that blocks a clip from sliding from the distal end of the catheter 35 to the proximal end of the catheter 35.

The sheath 324 may have two lumens running longitudinally therethrough. These lumens may include a first lumen 324a and a second lumen 324b running from a distal end to a proximal end of the sheath 324. Two endoscopic instruments with grasper end effectors, a first grasper 326a, and a second grasper 326b, may be delivered to the access site 55 through the lumens of the sheath 324. The grasper end effectors may include any instrument, for example, forceps, barbed needles, etc., configured to grasp any object within the body. In some embodiments, the first grasper 326a may be delivered to the access site 55 through the first lumen 324a, and the second grasper 326b through the second lumen 324b. It is also contemplated that, in some embodiments, both graspers may be delivered to the access site 55 through the same lumen. The graspers may also be extracted from the access site 55 through the lumens. Linkages 322a and 322b may connect the first grasper 326a and the second grasper 326b, respectively, to one or more actuation mechanisms at the proximal end of the endoscope 10. These actuation mechanisms may operate the graspers at the access site 55. Operating the graspers may include translating and rotating the graspers at the access site 55, and moving jaws of the grasper to grasp cut/separated tissue edges between these jaws.

Figure 8B:
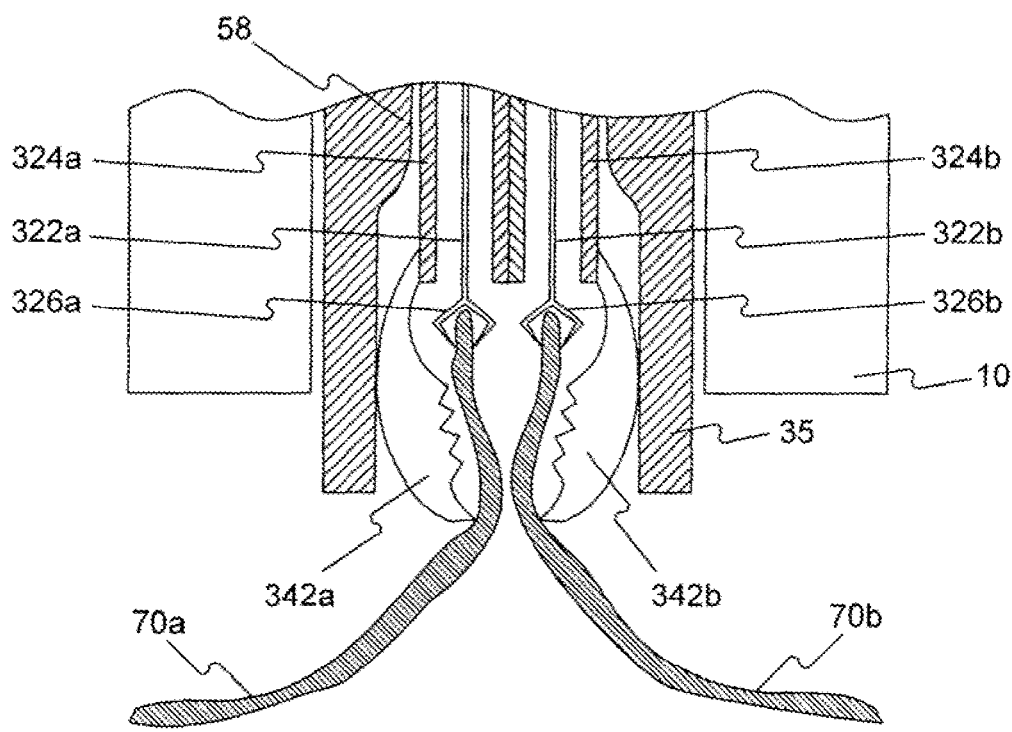

At the access site 55, each grasper may be maneuvered to the location of a piece of tissue. The first grasper 326a may grasp the first tissue edge 70a and the second grasper 326b may grasp the second tissue edge 70b. The graspers, along with the tissue, may then be retracted from the access site 55. The sheath 324 may also be pulled into the catheter 35, pulling the grasped tissue edges and the clip 340 along with it. FIG. 8B illustrates the retraction of the sheath 324 into the catheter 35. During retraction, the movement of the clip 340 may be blocked by the flange 58. Continued retraction of the sheath 324 may plastically deform the jaws of the clip 340 by forcing them together. The first tissue edge 70a and the second tissue edge 70b may be trapped between the deformed jaws, thereby joining the tissue edges together. The actuation device may then be activated to release the tissue edges from the graspers 326a, 326b.

In some embodiments, multiple clips 340 may be mounted on the surface of sheath 324 (as described with reference to clip 40 shown in FIGS. 2A-3H). After a first clip is deployed, another clip 340 may slide down the sheath 324 and extend out of the distal end of the catheter 35. This second clip may be used to join tissue edges as described earlier.

Figure 9A:
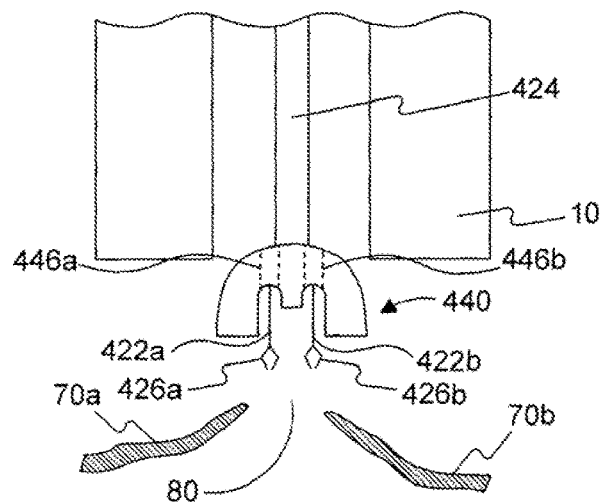
FIGS. 9A-9D are illustrations of another embodiment of a clip and a method of using a clip.

FIGS. 9A-9D illustrate another embodiment of a clip that may be used to close aperture 80. Clip 440 of this embodiment may be delivered to the access site 55 at the distal end of an elongate member 424 extending from a working lumen of the endoscope. Similar to graspers 326a, 326b of the embodiment in FIGS. 8A-8B, a first grasper 426a and a second grasper 426b may also be delivered to the access site 55 through the elongate member 424. The graspers 426a, 426b may be operated at the access site 55 by one or more actuation mechanisms external to the body. FIG. 9A illustrates clip 440 positioned at the access site 55. The graspers 426a, 426b may extend to the access site 55 through holes or cavities in clip 440. In some embodiments, the first grasper 426a may extend into the access site 55 through a first through-hole 446a and the second grasper 426b may extend into the access site 55 through a second through-hole 446b. It is also contemplated that, in some embodiments, both the first and the second graspers may extend through the same through-hole.

Figure 9B:
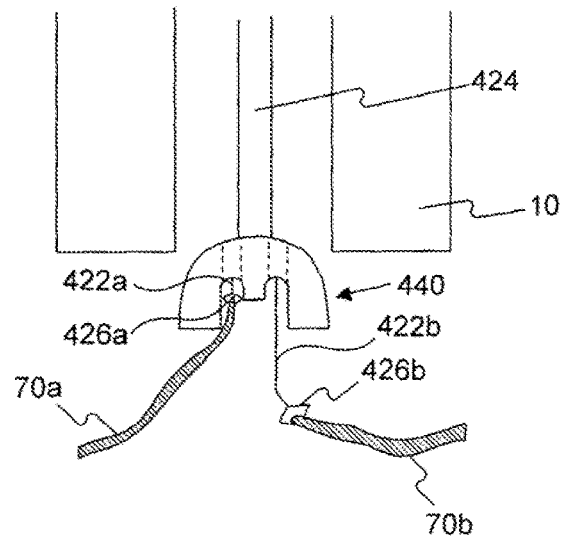
Figure 9C:
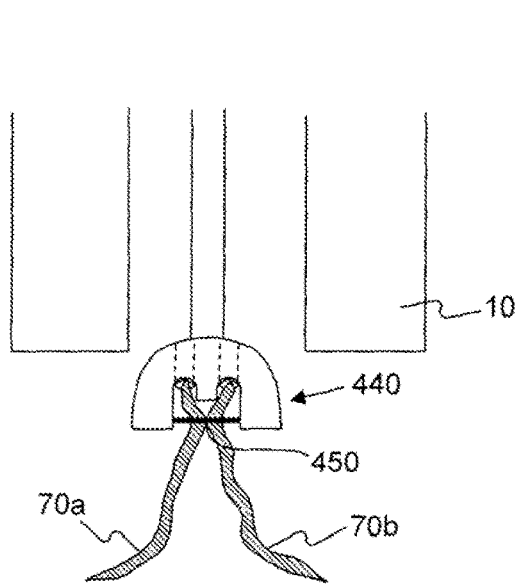
Figure 9D:
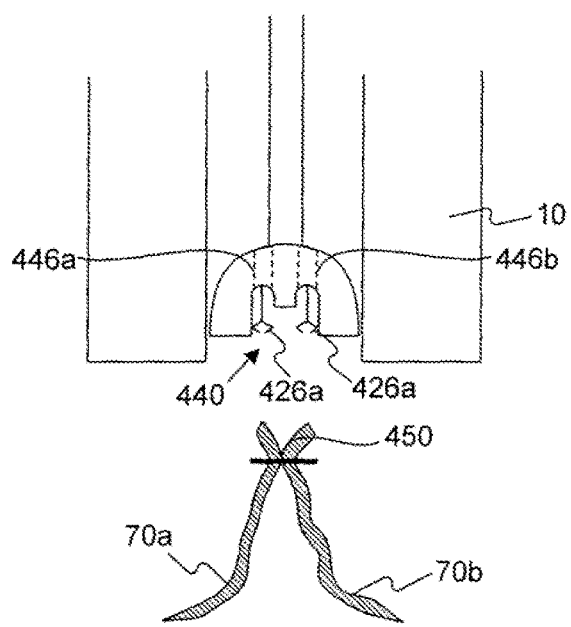

As described with reference to FIG. 8B, the first grasper 426a may grasp the first tissue edge 70a and draw it into clip 440 and the second grasper 426b may grasp the second tissue edge 70b and draw it into the clip 440. The tissue edges may be drawn into the clip by retracting the grasper into the elongate member 424, FIG. 9B illustrates a view of clip 440 with the first and second tissue pieces grasped by the graspers. When both tissue edges are drawn into the clip 440, the actuation mechanism may be activated to release a fastener 450 to bind the tissue edges together. Fastener 450 may include a barb or any object configured to join the tissue edges. In some embodiments, the fastener 450 may be released from the side of clip 440 and may penetrate the first and second tissue pieces to join them together. However, it is also contemplated that fastener 450 may be released from the clip in another manner. FIG. 9C illustrates the fastener 450 joining the two tissue edges together. After the tissue edges are securely bound together, the fastener 450 may be released from the clip 440. In some embodiments, the fastener 450 may be released by activating the actuation mechanism. It is also contemplated that, in some embodiments, the clip 440 may be retracted after joining the tissue edges together, and the staple may be pulled off the clip by the force of the stretched stomach wall. FIG. 9D illustrates a view of the released fastener 450 joining the two tissue edges together.

Figure 10:
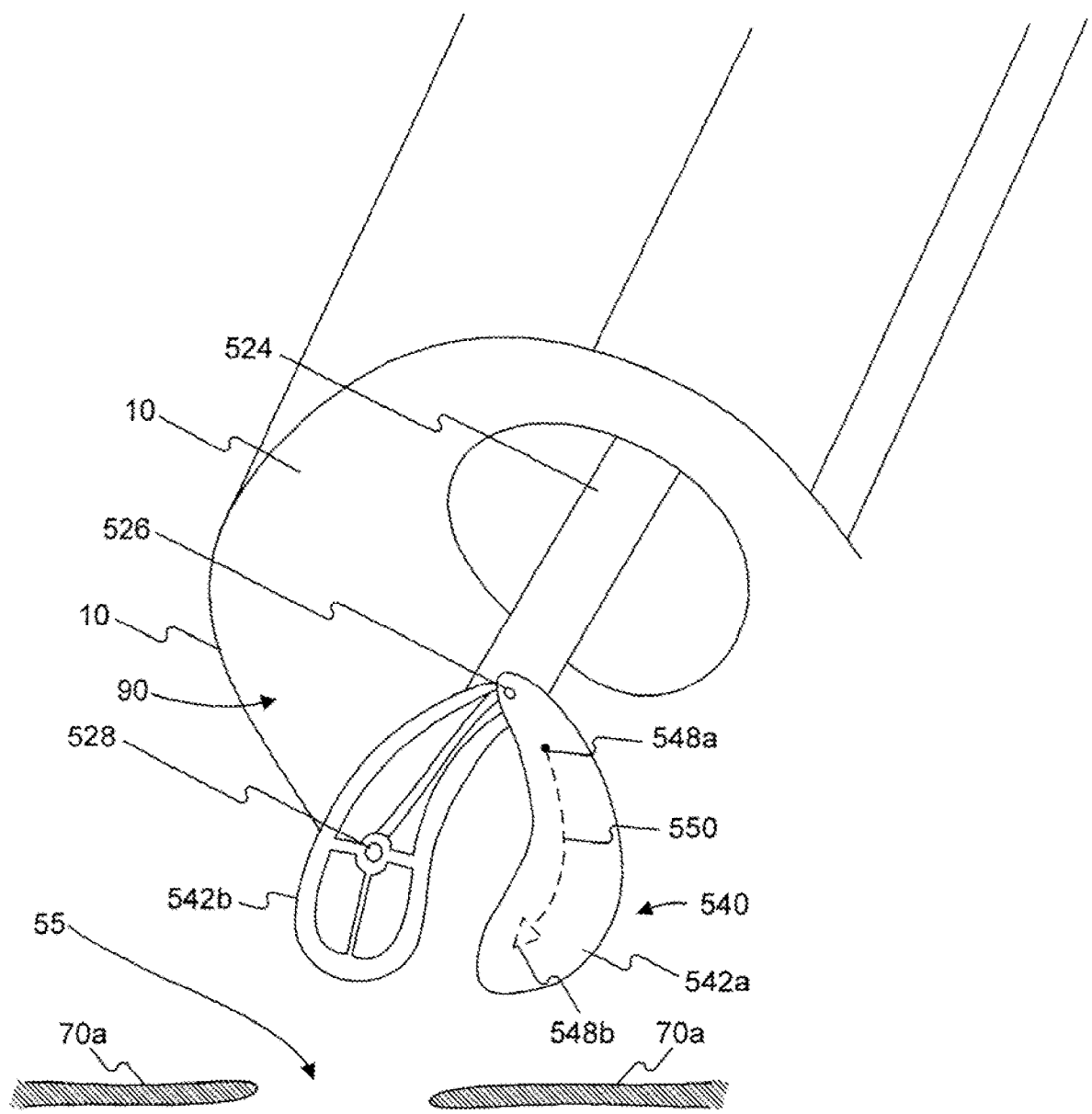
FIG. 10 is a schematic view of another embodiment of a clip.

FIG. 10 illustrates an embodiment of a clip having an attached barb 550. The clip 540 attached to an elongate member 524 may be delivered to the access site 55 through the working lumen of the endoscope 10. As in previously described embodiments, the clip 540 may transform to an open configuration as it extends from the distal end 90 of the endoscope 10. The clip 540 may include a first jaw 542a and a second jaw 542b connected at a hinge 526. The elongate member 524 may include linkages that connect the jaws to an actuation mechanism outside the body. The actuation mechanism may be configured to move the jaws of clip 540 towards each other and, thereby, form a closed configuration.

A barb 550 may be attached to one of the jaws, for instance, the first jaw 542a, of clip 540. The barb 550 may be hinged to the first jaw 542a at a first end 548a. The second end 548b of the barb 550 may form a sharp point or an arrowhead. In some embodiments, barb 550 may also include spikes (similar to spikes 652 on barb 650 of FIG. 12A) that protrude from a surface of the barb 550. The barb 550 may be spring loaded and the second end 548b of the barb 550 may be retained on the first jaw 542a by a catch or another mechanism. The actuation device may be configured to release the catch. Upon release of the catch, the barb 550 may be configured to transform to a deployed configuration. In the embodiment of clip depicted in FIG. 10, the barb 550 may rotate about the first end 548a and snap to a second configuration (as seen in FIG. 11B). In the second configuration, the second end 548b of the barb 550 may project from the first jaw 542a and point towards the second jaw 542b.

The second jaw 542b may have a hole 528 to enable the second end 548b of the barb to protrude through when the clip 540 is in a closed configuration. The second jaw 542b may also features designed to impart some compliance to the second jaw 542b. In FIG. 10, these compliant features are depicted as slender members arranged as a cross-hair around the hole 528. These members may bend slightly when an out of plane force is applied on the members, thereby providing compliance to the second jaw 542b. The purpose of the compliance will become clearer in the discussion in reference to the operation of clip 540. In some embodiments, other forms of compliance enhancing features may be incorporated into the second jaw 542b. It is also contemplated that, in some embodiments, the compliance enhancing features may be eliminated.

Figure 11A:
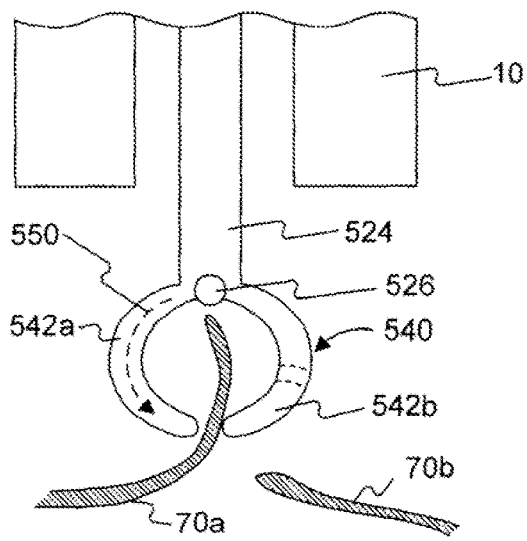
FIGS. 11A-11E are illustrations of an exemplary method of using a clip.
Figure 11B:
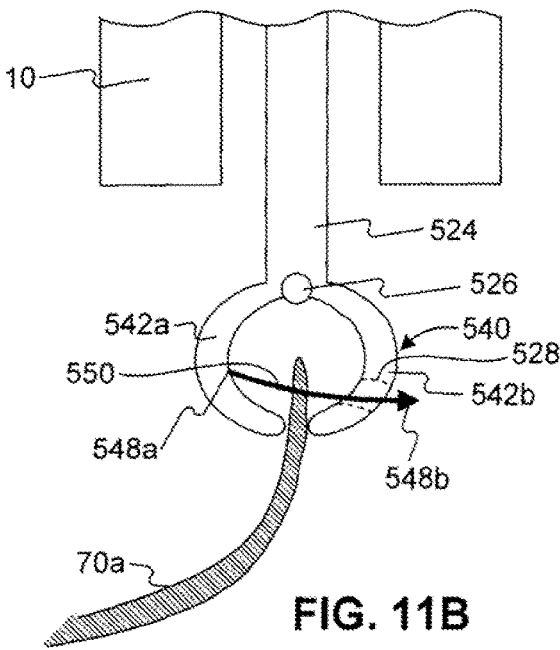

FIGS. 11A-E illustrate the use of clip 540 to approximate tissue edges (for example, first tissue edge 70a and second tissue edge 70b), and close aperture 80. The endoscope 10 may be maneuvered to locate the first tissue edge 70a between the open jaws of clip 540. The actuation device may then be actuated to grasp the first tissue edge 70a by closing the jaws. FIG. 11A depicts a view of clip 540 with the first tissue edge 70a grasped between its jaws. With the tissue firmly grasped, the barb 550 may be released from the first jaw 542a. Releasing the barb 550 may rotate, or otherwise actuate, the spring loaded barb 550 about the first end 548a to the second configuration. While moving to the second configuration, the sharp second end 548b may pierce through the grasped first tissue edge 70a. FIG. 11B depicts a view of the clip 540 with the grasped first tissue edge 70a pierced by the barb 550. In some embodiments, the grasped tissue may be forced against the surface of the second jaw 542b while the barb tries to pierce through the tissue from the opposite side. Compliance enhancement features of the second jaw 542b may enable the barb 550 to pierce the tissue without undue trauma.

Figure 11C:
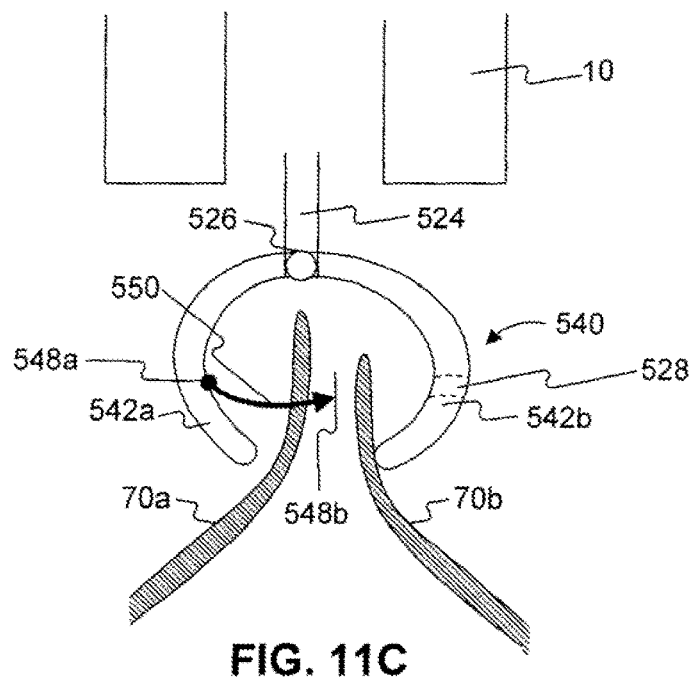
Figure 11D:
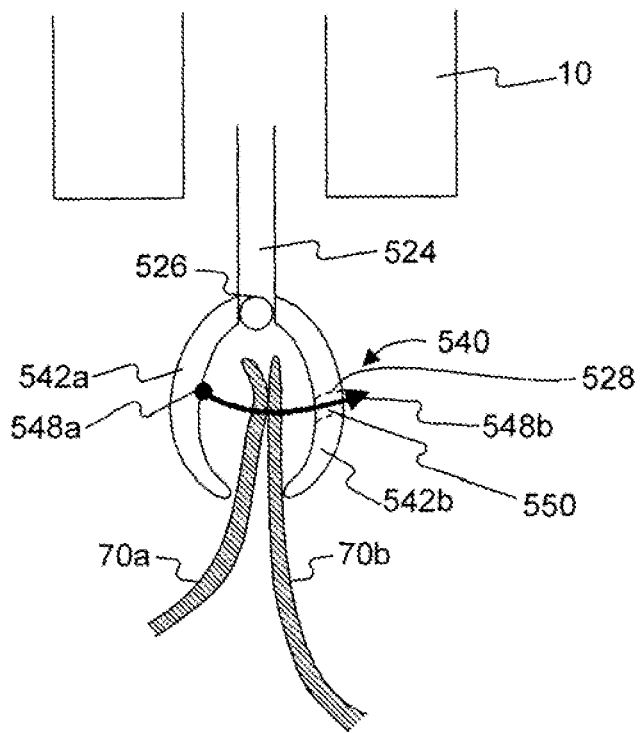
Figure 11E:
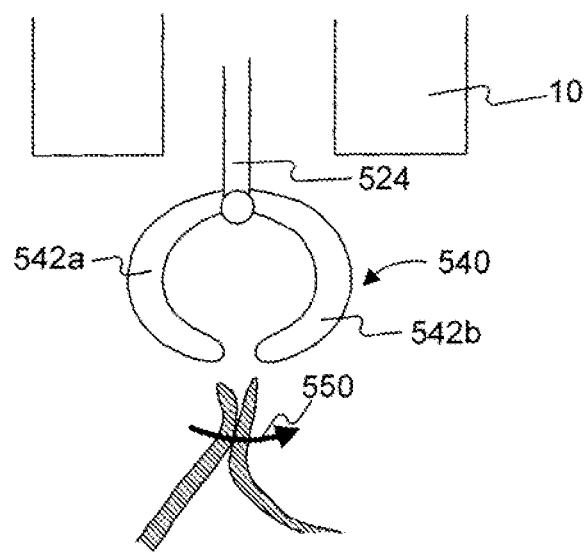

The clip 540 may again be opened using the actuation mechanism. FIG. 11C illustrates a view of clip 540 with the jaws open. The shape of the second end 548b may prevent the pierced first tissue edge 70a from being released when the jaws of the clip 540 are opened. The endoscope may again be maneuvered to position the second tissue edge 70b between the jaws of clip 540. The jaws may now be closed to grasp the second tissue edge 70b between the jaws. When the jaws rotate to the closed configuration, the pointed second end 548b of the barb 550 may pierce the second tissue edge 70b. FIG. 11D depicts the clip 540 with both tissue edges pierced by the barb 550. The clip 540 may again be opened and barb 550 detached from the first jaw 542a to release the tissue edges joined together by the barb 550. FIG. 11E illustrates the tissue pieces joined by the barb 550. In some embodiments, the barb 550 may be detached by releasing the first end 548a from the first jaw 542a using the actuation mechanism. In embodiments of clip 540 with spikes on the barb 550, these spikes may assist in preventing the tissue edges from slipping off the barb 550. In some embodiments, retracting the clip away from the access site 55 may stretch the organ wall 70. The stretched organ wall may then pull the first end 548a off the first jaw 542a.

In some embodiments, the entire clip 550 may be released from the elongate member 524 after the tissue edges are joined together with the barb. Releasing the clip 540 may be accomplished by the actuation device or the force exerted by the stretched organ wall 70.

Figure 12A:
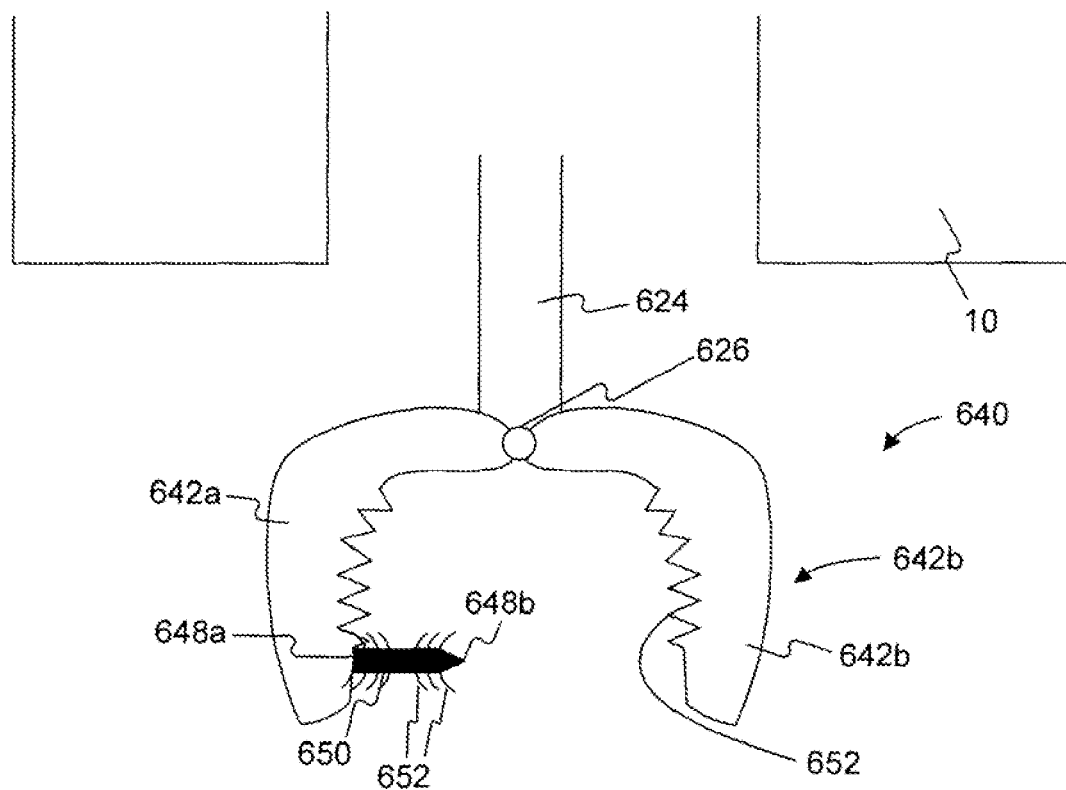
FIGS. 12A-12E are illustrations of another embodiment of a clip and a method of using a clip.

FIGS. 12A-12E illustrate another embodiment of a clip with a barb 650 used to join cut/separated tissue edges. In the embodiment of FIG. 12A, the clip 640 may include a first jaw 642a and a second jaw 642b attached together at a hinge 626. Clip 640 may be delivered and operated at the access site 55 similar to clip 540 of the previous embodiment. A barb 650 may be attached to the first jaw 642a at a first end 648a. The first end 648a may be pointed and may be retained on first jaw 642a by a catch or other retention features on first jaw 642a. The second end 648b of the barb 650 may project from the first jaw 642a and point towards the second jaw 642b. The second end 648b of the barb 650 may also be pointed. The second jaw 642b may also include retention features that are configured to couple to the second end 648b and retain the barb 650 to the second jaw 642b. The barb 650 may also include spikes 652 on its surface. The barb 650 may include spikes 652 pointed to both the first end 648a and the second end 648b.

Figure 12B:
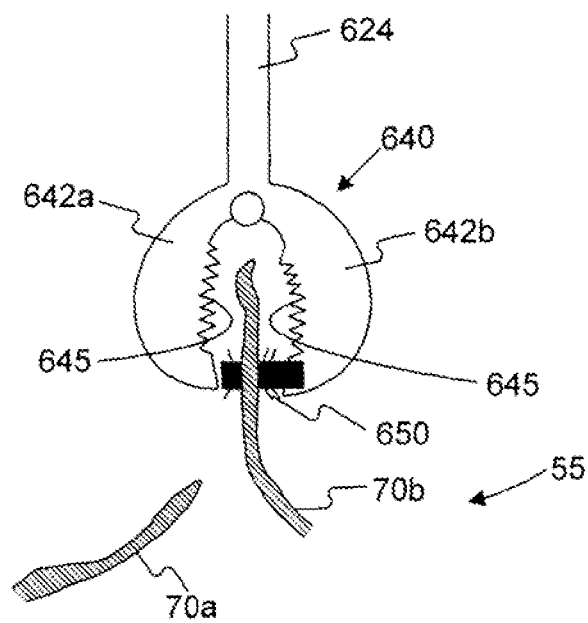
Figure 12C:
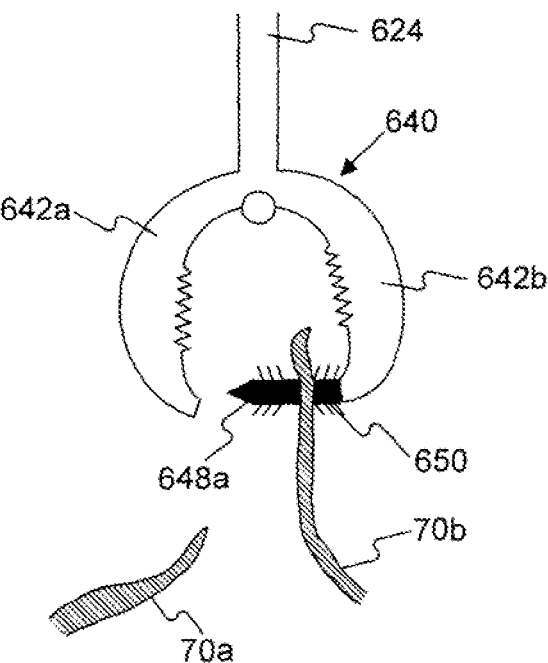
Figure 12D:
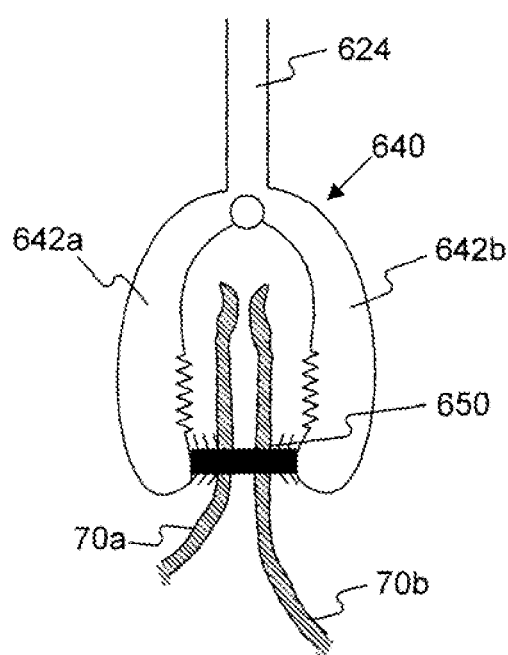
Figure 12E:
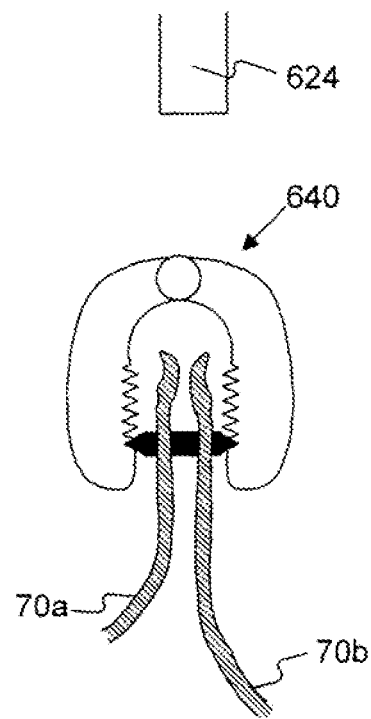

The second tissue edge 70b may be positioned between the jaws of the clip 640 and the jaws closed. While closing, the barb 650 may pierce through the second tissue edge 70b. FIG. 12B illustrates a view of clip 640 with the grasped second tissue edge 70b. While in the closed configuration, the second end 648b of the barb 650 may engage with the retention features on the second jaw 642b. The jaws may again be opened to grasp the first tissue edge 70a. FIG. 12C illustrates a view of the clip 640 with the jaws opened. Barb 650 may now be retained by the retention features of the second jaw 642b. The spikes 652 on the barb 650 may prevent the second tissue edge 70b from being released when the jaws are opened. The first tissue edge 70a may be positioned between the jaws and the jaws closed again to grasp the first tissue edge 70a. FIG. 12D illustrates the first and second tissues grasped between the jaws of clip 640. The sharp first end 648a of barb 650 may pierce through the first tissue edge 70a when the jaws are closed. The barb 650 may thus pierce through and join the first tissue edge 70a and second tissue edge 70b. As in the previous embodiment, the clip 640 may now be opened and the barb 650 released from the clip 640. The barb 650 may keep first tissue edge 70a and second tissue edge 70b joined. In some embodiments, the entire clip 640 may be released from the elongate member 624 to leave behind the clip 640 joining the two tissue edges together.

FIGS. 13A-13E illustrate another embodiment of a clip used to attach tissue edges. As in embodiments above, clip 740 may also include a first jaw 742a and a second jaw 742b connected by a hinge 726. Clip 740 attached to an elongate member 722 may also be delivered to the access site 55 through the working lumen of an endoscope 10 and may be operated by an actuation mechanism external to the body. As in clip 40, clip 740 may also include a hollow through-hole 746 at a location between the jaws.

A claw 750 attached to a flexible part 724 may be delivered to the access site 55 through the through-hole 746. The flexible part 724 may be manipulated external to the body to control the claw 750 at the access site 55. With the jaws of the clip 740 open, the claw 750 attached to the flexible part 724 may be advanced through an aperture 80. FIG. 13B shows the claw 750 on an opposite side of the puncture. The flexible part 724 and the claw 750 may now be retracted into the elongate member 722. The claw 750 may snag and drag the aperture 80 along with the first tissue edge 70a and second tissue edge 70b into clip 740. Claw 750 may have any shape configured to snag the tissue edges and draw them into the clip 740.

Figure 13A:
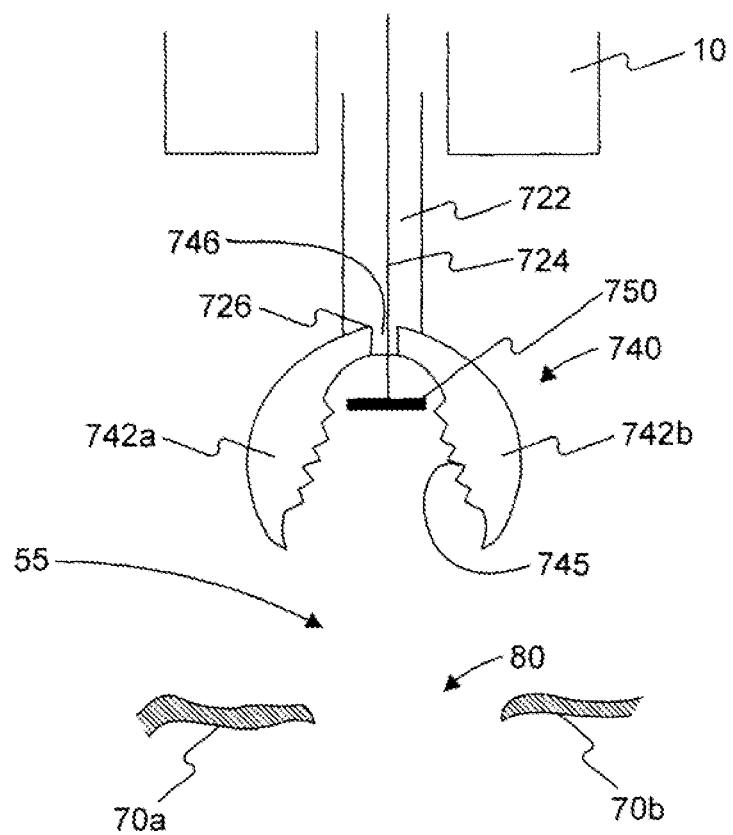
FIGS. 13A-13E are illustrations of another embodiment of a clip and a method of using a clip.
Figure 13E:
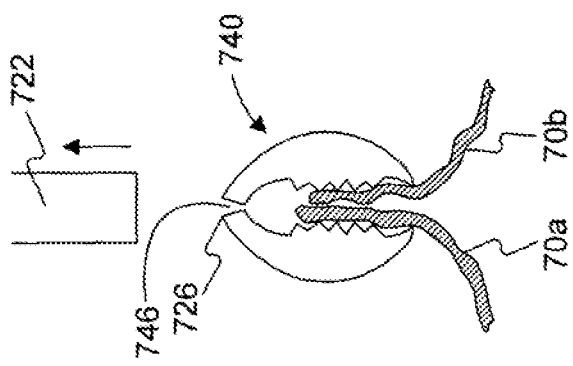
Figure 13D:
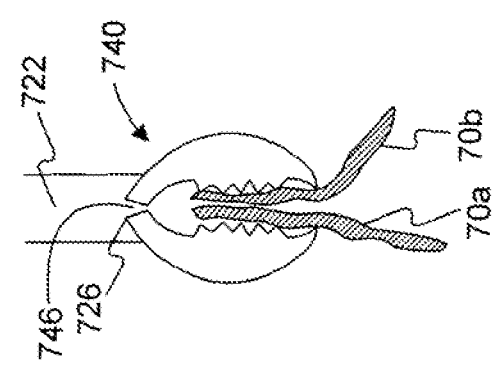
Figure 13C:
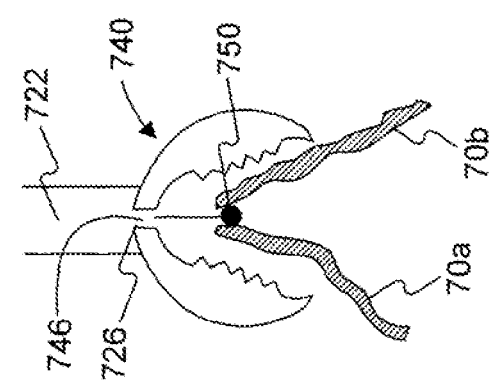
Figure 13B:
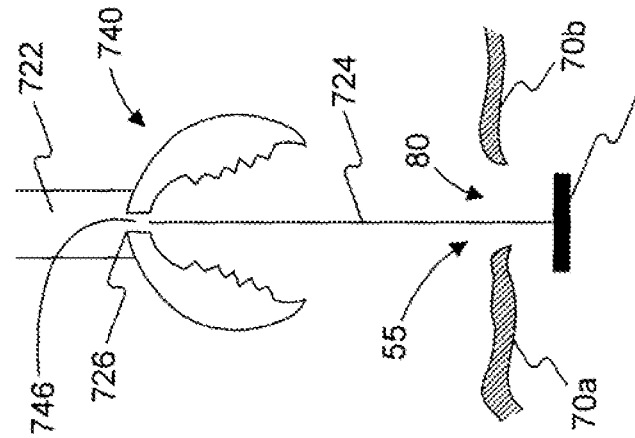

FIG. 13C illustrates a view of the clip 740 with the snagged stomach wall positioned between its jaws. Once the first tissue edge 70a and the second tissue edge 70b are appropriately positioned between the jaws, clip 740 may be closed. FIG. 13O illustrates the clip 740 in a closed configuration. The closed clip 740 may grasp the tissue edges, thereby joining them together. The clip 740 may now be released and the endoscope retracted from within the body.

FIGS. 14A-14F illustrate another embodiment of a clip 840 used to fasten first tissue edge 70a and second tissue edge 70b at access site 55. Clip 840 may be comprised of multiple arms, for instance, a first arm 842a and a second arm 842b. Although clip 840 is depicted with two arms, different embodiments of clip 840 may have a different number of arms. Clip 840 may also include a center arm 850 positioned between first arm 842a and second arm 842b. Center arm 850 may include a barb 858 positioned thereon, in some embodiments, barb 858 may be positioned at a distal end of center arm 850. Although in FIG. 14A, barb 858 is shown as a projection on center arm 850, barb 858 may have any shape and configuration. For instance, barb 858 may be sharp and needle shaped in some embodiments. First arm 842a and second arm 842b may be attached to the center arm 850 at attachment sections 846a and 846b respectively, at a proximal region of the center arm 850. Any attachment mechanism may be used to attach the first and second arms 842a and 842b to the center arm 850. Proximal to attachment sections 846a and 846b, center arm 850 may include protrusions 852a and 852b extending in a radial direction. In some embodiments, these protrusions may be spring loaded. In these embodiments, the protrusions 852a and 852b may be configured to compress or depress inwards towards center arm 850 upon the application of a radially inward force. In other embodiments, protrusions 852a and 852b may not be spring loaded, but may be otherwise configured to move towards the center arm 850 upon the application of a radially inward force. For example, protrusions 852a and 852b may be comprised of a compressible material.

From their respective attachment sections at the proximal region of center arm 850, the first and second arms 842a and 842b may extend a distance longitudinally, and distally, along the length of center arm 850. The first and second arms 842a and 842b may then be bent away from the center arm 850 such that distal regions of these arms make an angle with a distal region of center arm 850. The first arm 842a may be bent away from the center arm 850 at a first section 844a, and the second arm 842b may be bent away from center arm 850 at a second section 844b. The first section 844a may be displaced longitudinally, or offset, from second section 844b.

A push-rod 822, coupled to a proximal end of clip 840, may be configured to extend the clip 840 from the distal end of a catheter 835 or an endoscope to access site 55. Actuating the push-rod 822 in a distal direction may move the push-rod 822 into the body, and may extend clip 840 out of the distal end of catheter 835. Actuating the push-rod in a proximal direction may retract the distal end of the push-rod 822 along with clip 840 into the catheter 835.

Clip 840 may also include an end cap 860 positioned at a proximal end of first and second arms 842a and 842b. The push-rod 822 may pass through a through-hole 866 on an end piece 864 positioned at a proximal end of the end-cap 860, to couple with the proximal end of clip 840. In some embodiments, end piece 864 may be integral with end cap 860, while in other embodiments, end piece 864 may be a part separate from end cap 860. Although end cap 860 may be fitted with the end piece 864 by any means, in some embodiments, the end piece 864 may be interference fitted with the proximal end of the end cap 860. Actuating push-rod 822 in a proximal direction may pull clip 840 at least partially into end cap 860. As clip 840 slides into end cap 860, the walls of the end cap 860 may contact the first and second arms 842a and 842b, and apply a radially inward force on the arms. This radially inward force may deflect these arms towards center arm 850. Since first section 844a and second section 844b of the two arms are longitudinally displaced from each other, end cap 860 may contact and deflect one of these arms towards the center arm 850 at least partially before contacting and deflecting the other arm towards the center arm 850.

Figure 14B:
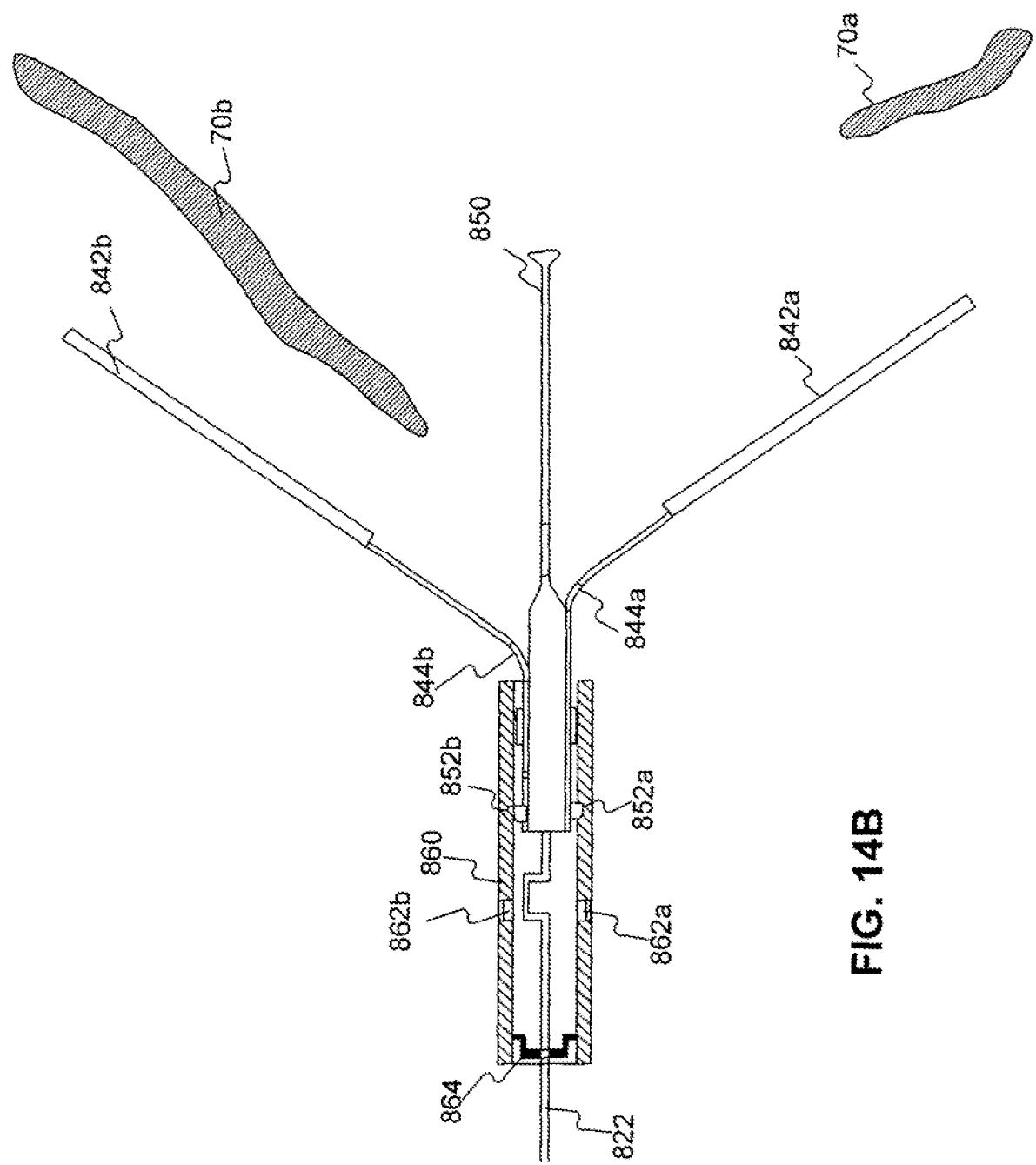
Figure 14C:
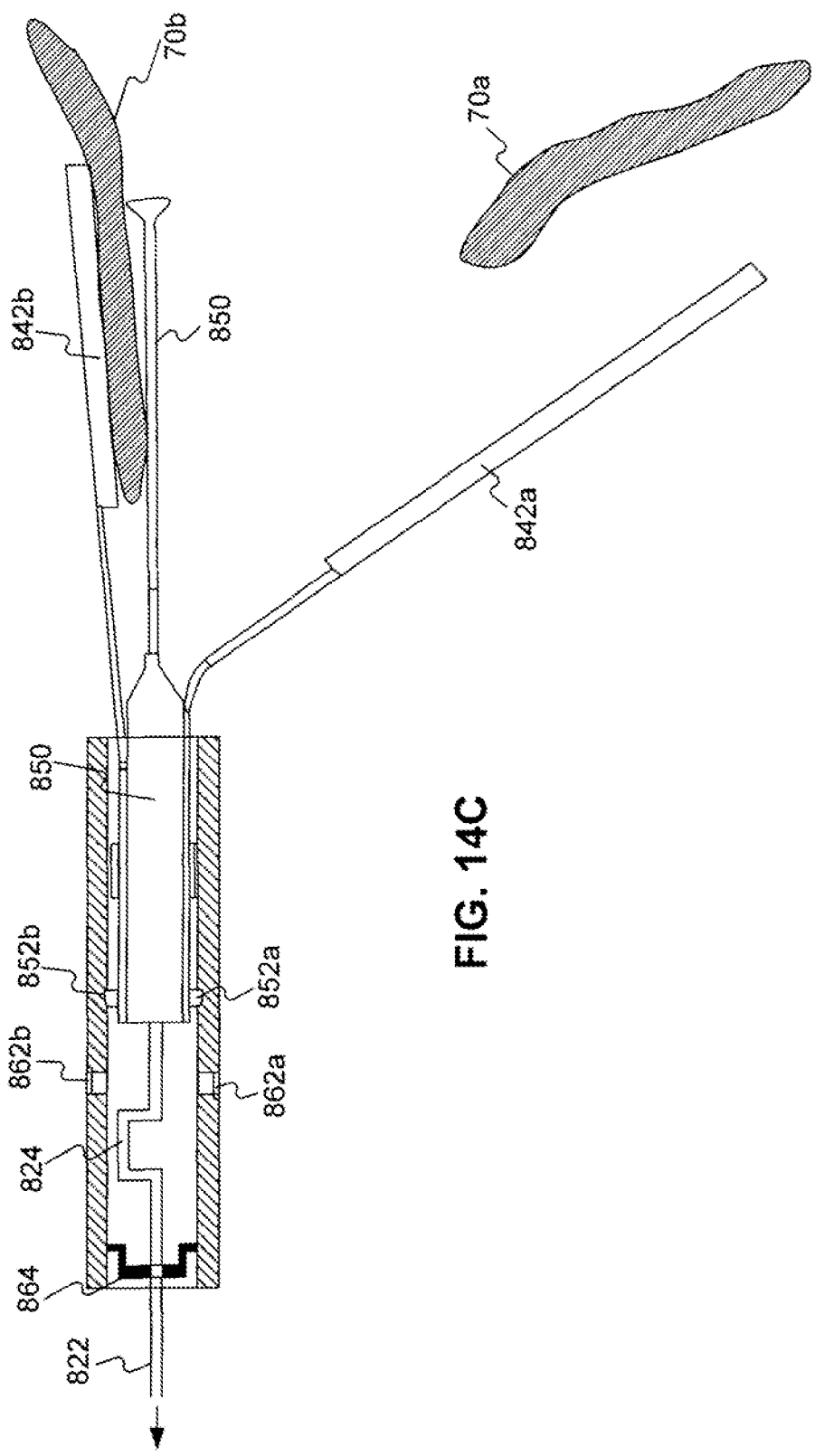

FIG. 14B illustrates a configuration of clip 840 with clip 840 partially retracted into end cap 860. In the embodiment of clip 840 illustrated in FIG. 14b, the end cap 860 contacts and deflects the second arm 842b towards center arm 850 before the end cap 860 contacts the first arm 842a. When used in a procedure to fasten tissue segments 70a and 70b, endoscope 10 or catheter 835 with clip 840 may be maneuvered to locate one of these tissue edges, for example second tissue edge 70b in FIG. 14b, between center arm 850 and second arm 842b. The push-rod 822 may then be actuated in a proximal direction to retract clip 840 partially into end cap 860. As the clip 840 slides within end cap 860, internal walls of the end cap 860 may slide on the protrusions 852a and 852b, and apply a radially inward force on these protrusions. This radially inward force may depress the protrusions 852a and 852b radially inwards towards center arm 850, thereby allowing the clip 840 to slide within end cap 860. Walls of end cap 860 may also contact and apply a radially inward force on second arm 842b to deflect the second arm towards center arm 850. As the second arm 842b deflects towards center arm 850, second tissue edge 70b may get held between these arms, FIG. 14C illustrates an embodiment of clip 840 with second tissue edge 70b held between center arm 850 and second arm 842b.

Figure 14D:
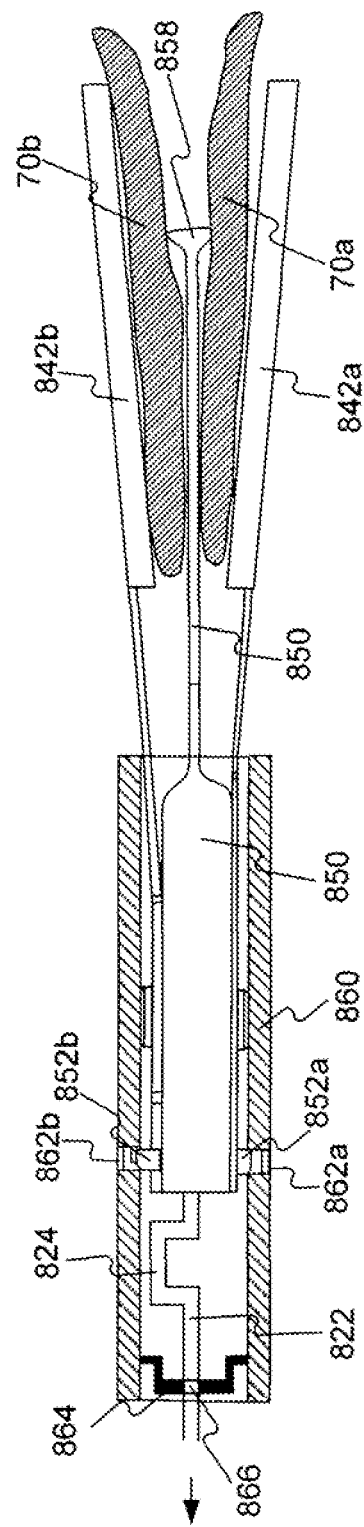

The distal end of endoscope 10 or catheter 835 may then be repositioned so that another tissue edge, for instance first tissue edge 70a, may be positioned between first arm 842a and center arm 850. Further actuation of the push-rod 822 towards the proximal end may move the clip 840 further into end cap 860. As the clip 840 moves further into the end cap 860, walls of the end cap 860 may contact and deflect the first arm 842a towards the center arm 850 with first tissue edge 70a between the first arm 842a and center arm 850. Further actuation of the push-rod 822 towards the proximal end may engage the protrusions 852a and 852b of center arm 850 with mating features 862a and 862b on end cap 860. In some embodiments, mating features 862a and 862b may be cavities in end cap 860 that are dimensioned to fit the protrusions 852a and 852b therein. Alignment of the protrusions with the mating features may relieve any constraining force from the protrusions, and allow the protrusions to spring back, or recover, to their original pre-depressed configuration. Engagement of the protrusions 852a and 852b with the mating features on end cap may lock the first and second arms 842a and 842b in a closed configuration, where these arms press against center arm 850 with the first and second tissue pieces 70a and 70b firmly grasped between them. In embodiments where center arm 850 includes a barb 858, the barb 858 may also assist in firmly securing the tissue edges between the arms. FIG. 14D illustrates an embodiment of clip 840 with the arms locked in a closed configuration.

Figure 14E:
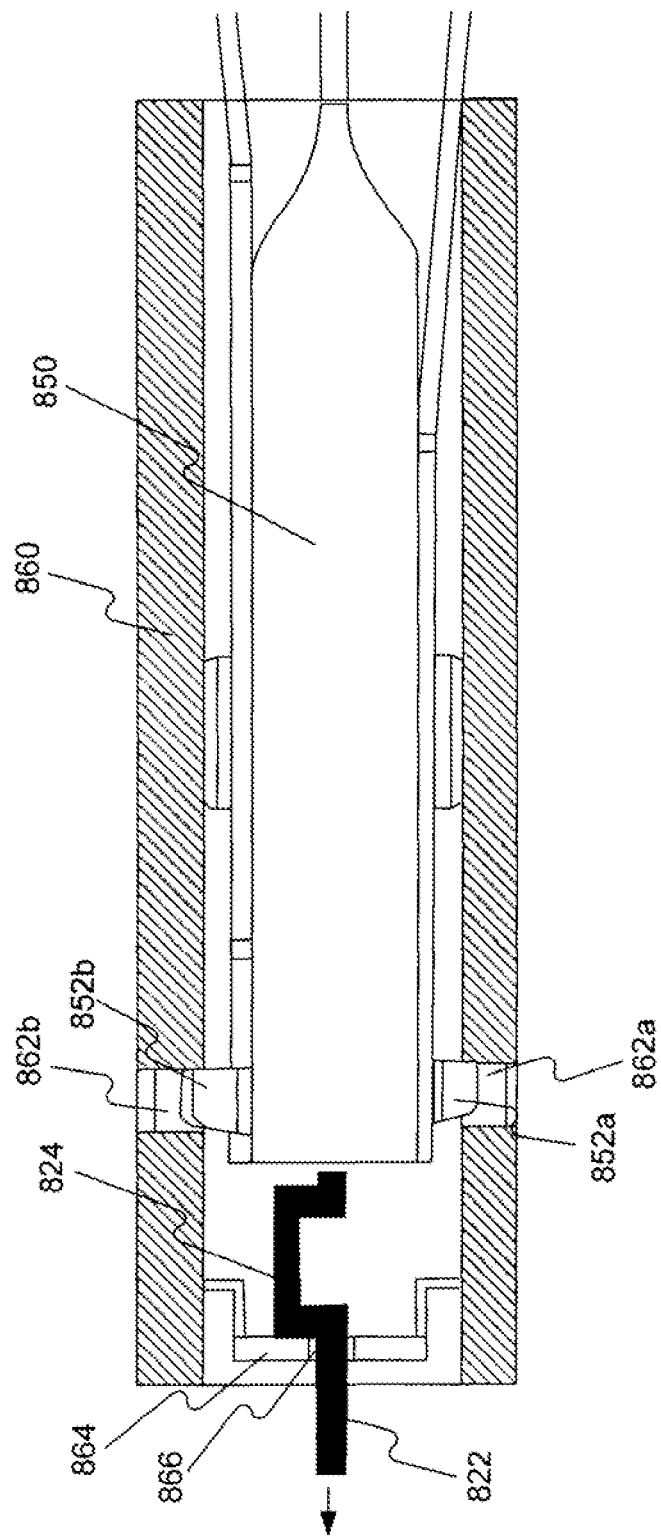

Engagement of the protrusions 852a and 852b with the mating features 862a and 862b on end cap 860 may also prevent the clip 840 from sliding further into the end cap 860 upon further actuation of the push-rod 822 towards the proximal end. Further actuation of push-rod 822 may stretch organ wall 70 and exert a force on the proximal end of clip 840. This force may detach the distal end of push-rod 822 from the proximal end of clip 840. As in other embodiments, any clip release mechanism (such as, threaded connections, frangible link, electrolysis link, etc.) may be used to separate push-rod 822 from the clip 840. FIG. 14E illustrates an embodiment of clip 840 with the push-rod 822 detached from clip 840.

Figure 14F:
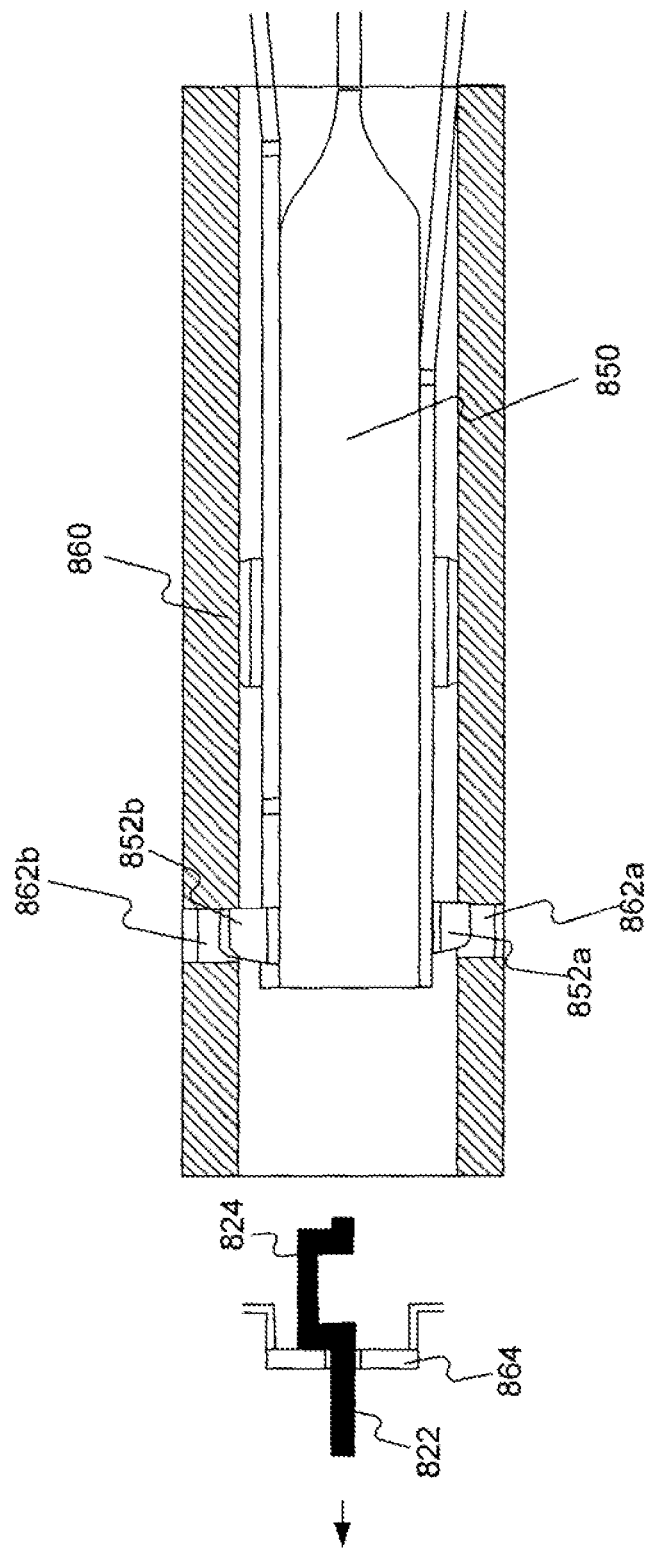

After the push-rod 822 detaches from clip 840, further retraction of the push-rod 822 towards the proximal end may cause a protrusion 824 on the push-rod 822 to abut against end piece 864. In some embodiments, the push-rod 822 and end cap 860 may be dimensioned such that protrusion 824 of the push-rod abuts against end piece 864 when the push-rod 822 detaches from clip 840. Although protrusion 824 is depicted as a bend in push-rod 822, the protrusion 824 may be of any form. Further actuation of the push-rod 822 may force the protrusion 824 against end piece 864 and cause the end piece 864 to be dislodged from the proximal end of the end cap 860. FIG. 14F illustrates an embodiment of clip 840 with the end piece 864 separated from end cap 860. The push-rod 822 may now be retracted out of the body through the catheter or endoscope.

Other methods may also be used to disengage the push-rod 822 from the end cap 860. In some embodiments, through-hole 866 may be configured to allow the push-rod 822 to be rotated and extracted from the end cap 860. For example, the through-hole 866 may have two different cross-sectional shapes along two directions. In these embodiments, a cross-section of the through-hole along one direction may correspond to a diameter of the push-rod 822, and the cross-section of the through-hole along another direction may correspond to the thickest region of the protrusion 824. Rotating the push-rod 822 to align protrusion 824 with the direction having a matching cross-section of the through-hole will allow the push-rod to be removed from end cap 860. In some embodiments, the protrusion 824 may be a c-shaped bend on push-rod 822 and the through-hole 866 cross-sectional shapes along two different directions may correspond to a diameter of the push-rod 822 and a dimension of the c-shaped bend on push-rod 822. In such an embodiment, rotation of the push-rod 822 may extract the push-rod 822 through the through-hole 866. In some embodiments, rotation of the push-rod 822 may retract the push-rod 822 partly through the through-hole 866 and engage the end piece 864 with the push-rod 822. In these embodiments, further actuation of the push-rod 822 may detach the end piece 864 from the end cap 860, leaving clip 840 in a locked configuration grasping the first and second tissue edges 70a and 70b.

It will be apparent to those skilled in the art that various modifications and variations can be made in the disclosed systems and processes without departing from the scope of the invention. For instance, an adhesive, tissue growth promoter, or another agent may be used in conjunction with any clip to promote the fastening of the tissue edges or the healing process. Also, any part of the clip may be bioabsorbable or conduct heat and/or electricity to aid in tissue fastening or the healing process. Although the disclosure discusses several embodiments of a clip used in an endoscopic procedure, in general, clips of the current disclosure may be used to approximate tissue edges in any medical procedure, such as in conventional surgery or other types of medical procedures. Other embodiments of the invention will be apparent to those skilled in the art from consideration of the specification and practice of the invention disclosed herein. It is intended that the specification and examples be considered as exemplary only, with a true scope of the invention being indicated by the following claims.

What is claimed is:

1. A medical device, comprising:
   a delivery member including a first arm and a second arm at a distal end of the delivery member, each of the first arm and the second arm being separately movable toward and away from a longitudinal axis of the delivery member, wherein the first arm is configured to grasp a first tissue edge by moving in a first direction relative to the longitudinal axis, and the second arm is configured to grasp a second tissue edge by moving in a second direction relative to the longitudinal axis, the second direction being opposite of the first direction; and
   a unitary clip positioned at the distal end of the delivery member and movable distally relative to the delivery member, wherein the unitary clip is configured to be released from the delivery member when the delivery member is pulled proximally, wherein the first arm and the second arm remain coupled to the delivery member after the unitary clip is released from the delivery member.

2. The medical device of claim 1, wherein the unitary clip includes a first jaw having teeth and a second jaw having teeth, wherein the first jaw and the second jaw of the unitary clip are disposed radially outward of the first arm and the second arm when the unitary clip is at the distal end of the delivery member.

3. The medical device of claim 2, wherein the unitary clip is in an open configuration when at the distal end of the delivery member, and upon release from the delivery member, the unitary clip is configured to be in a closed configuration where the teeth of the first jaw and the teeth of the second jaw are closer to a central axis of the unitary clip than when in the open configuration.

4. The medical device of claim 3, wherein the first tissue edge and the second tissue edge are configured to be secured to one another between the first jaw and the second jaw of the unitary clip while the unitary clip is in the closed configuration and separated from the delivery member.

5. The medical device of claim 1, wherein the first direction is away from the longitudinal axis of the delivery member.

6. The medical device of claim 1, wherein the second direction is away from the longitudinal axis of the delivery member.

7. The medical device of claim 1, further including a plurality of unitary clips positioned on the delivery member.

8. The medical device of claim 1, wherein the delivery member includes a rod.

9. The medical device of claim 1, wherein the unitary clip includes a through hole through which a portion of the delivery member is located.

10. A medical device, comprising:
a delivery member having a first arm and a second arm, wherein the first arm and the second arm are separately movable toward and away from a longitudinal axis of the delivery member; and
a clip positioned at the distal end of the delivery member and movable distally relative to the delivery member, the clip including an opening, wherein the clip is configured to be released from the delivery member when the delivery member is pulled proximally through the opening.

11. The medical device of claim 10, wherein the first arm and the second arm remain coupled to the delivery member after the clip is released from the delivery member.

12. The medical device of claim 10, wherein the first arm is configured to grasp a first tissue edge by moving in a first direction relative to the longitudinal axis, and the second arm is configured to grasp a second tissue edge by moving in a second direction relative to the longitudinal axis, the second direction being opposite of the first direction.

13. A medical device, comprising:
a delivery member including a first arm and a second arm at a distal end of the delivery member, each of the first arm and the second arm being separately movable toward and away from a longitudinal axis of the delivery member, wherein the first arm is configured to grasp a first tissue edge by moving in a first direction relative to the longitudinal axis, and the second arm is configured to grasp a second tissue edge by moving in a second direction relative to the longitudinal axis, the second direction being opposite of the first direction; and
a unitary clip positioned at the distal end of the delivery member and movable distally relative to the delivery member, wherein the unitary clip is configured to be released from the delivery member when the delivery member is pulled proximally, wherein the unitary clip includes a through hole through which a portion of the delivery member is located.

14. The medical device of claim 13, wherein the unitary clip includes a first jaw having teeth and a second jaw having teeth, wherein the first jaw and the second jaw of the unitary clip are disposed radially outward of the first arm and the second arm when the unitary clip is at the distal end of the delivery member.

15. The medical device of claim 14, wherein the unitary clip is in an open configuration when at the distal end of the delivery member, and upon release from the delivery member, the unitary clip is configured to be in a closed configuration where the teeth of the first jaw and the teeth of the second jaw are closer to a central axis of the unitary clip than when in the open configuration.

16. The medical device of claim 15, wherein the first tissue edge and the second tissue edge are configured to be secured to one another between the first jaw and the second jaw of the unitary clip while the unitary clip is in the closed configuration and separated from the delivery member.

17. The medical device of claim 13, wherein the first direction is away from the longitudinal axis of the delivery member.

18. The medical device of claim 13, wherein the second direction is away from the longitudinal axis of the delivery member.

19. The medical device of claim 13, further including a plurality of unitary clips positioned on the delivery member.

20. The medical device of claim 13, wherein the delivery member includes a rod.

* * * * *